United States Patent [19]

Järvinen et al.

[11] Patent Number: 5,436,350
[45] Date of Patent: Jul. 25, 1995

[54] BISPILOCARPIC ACID ESTER DERIVATIVES AND PROCESS FOR THEIR PREPARATION

[76] Inventors: Tomi Järvinen, Sompatie 3 C 1; Pekka Peura, Retkeilijäntie 14 C 4; Pekka Suhonen, Retkeilijäntie 9 D 33, all of SF-70200 Kuopio; Arto Urtti, Kelokuja 11 B 10, SF-74200 Kuopio; Hannu Hanhijärvi, Palokärjenkatu 1 as 2, SF-20600 Turku; Esko Pohjala, Tohtorinkatu 7 B 6, SF-33720 Tampere, all of Finland

[21] Appl. No.: 67,674

[22] Filed: May 26, 1993

[63] Related application is a continuation-in-part of PCT/FI91/00359, Nov. 27, 1991.

[30] Foreign Application Priority Data

Nov. 30, 1990 [FI] Finland .................................. 905930
Nov. 27, 1991 [WO] WIPO ............... PCT/FIX91/00359
May 29, 1992 [FI] Finland .................................. 922518
May 29, 1992 [FI] Finland .................................. 922519

[51] Int. Cl.⁶ .................. C07D 233/64; C07D 405/14; A61K 31/415
[52] U.S. Cl. .............................. 548/312.7; 514/397; 514/399; 548/314.4; 548/341.5
[58] Field of Search ................ 548/314.4, 314.5, 312.7; 514/397, 399

[56] References Cited

U.S. PATENT DOCUMENTS

2,792,390 5/1957 Stromberg ...................... 548/314.4
4,061,722 12/1977 Bodor .................................. 514/397
4,661,602 4/1987 Myers et al. ...................... 548/314.4

FOREIGN PATENT DOCUMENTS

0106541 4/1984 European Pat. Off. ............ 514/397
2462801 11/1975 Germany .......................... 548/315.7

OTHER PUBLICATIONS

"0,0'-(1,4-Xylylene) Bispilocarpic Acid Esters As New Potential Double Prodrugs Of Pilocarpine For Improved Ocular Delivery, I. Synthesis And Analysis," Järvinen et al. I, International Journal of Pharmaceutics, 75 (1991) 249–258 (applicants' own publication, published after first priority date).
"0,0'-(1,4-Xylylene) Bispilocarpic Acid Esters As New Potential Double Prodrugs Of Pilocarpine For Improved Ocular Delivery, II. Physicochemical Properties, Stability, Solubility And Enzymatic Hydrolysis," Järvinen et al. II, International Journal of Pharmaceutics, 75 (1991) 249–258 (applicants' own publication, published after first priority date).
Chemical Abstracts, vol. 116 (1992), 27944m, Int. J. Pharm. 1991, 75 (2–3), s. 249–258 (eng.), Jarvinon et al. III.
Chemical Abstracts, vol. 1116, (1992), 98896h, Int. J. Quantum Chem., Quantum Biol. Symp. 1991, 18, s. 247–267 (eng.), Konschin et al.
Chemical Abstracts, vol. 116 (1992), 113412t, Pharm. Res. 1991, 8(12), s. 1539–1542 (eng.) Suhonen et al.
Chemical Abstracts, vol. 116 (1992), 221408e, Int. J. Pharm. 1992, 79(2–3), s. 243–50 (eng.), Jarvinen et al., IV.
Chemical Abstracts, vol. 116 (1992), 235600y, Int. J. Pharm. 1992, 79(2–3), s. 233–242 (eng.), Jarvinen et al., V.
Chemical Abstracts, vol. 116, Chemical Substance Index, s. 5184–5185 CS.
Chemical Abstracts, vol. 116 (1992), Formula Index, s. 4043F.

*Primary Examiner*—Floyd D. Higel

[57] ABSTRACT

The object of the invention are bispilocarpates useful in the treatment of glaucoma and having the formula

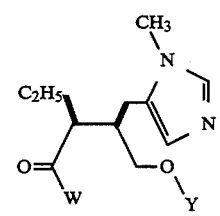

wherein A) Y is hydrogen or the acyl group (ABSTRACT CONTINUED ON NEXT PAGE.)

and W is the group —O—A—O—Z—Y′, wherein Y′ is hydrogen or the acyl group

the groups R and R′ having different meanings and may be the same or different and A is an aliphatic, aromatic or heterocyclic bridging group, and —Z—Y′ is

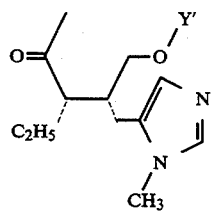

or B) W is OR, wherein R has the same meaning as above, Y is

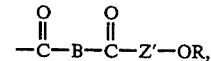

where R′ has the same meaning as above, B means the same as A and Z′—OR′ is

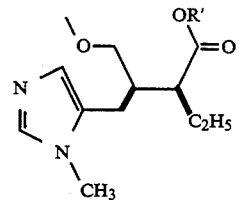

or C) W and Y together mean $$-O-A-O-Z-\overset{O}{\underset{\|}{C}}-B-\overset{O}{\underset{\|}{C}}-$$

where the symbols have the same meanings as above.

13 Claims, No Drawings

BISPILOCARPIC ACID ESTER DERIVATIVES AND PROCESS FOR THEIR PREPARATION

This application is a continuation-in-part of PCT/FI91/00359 having an international filing date of Nov. 27, 1991.

FIELD OF INVENTION

The present invention relates to novel pilocarpine prodrug compounds useful for the treatment of glaucoma, and specifically to bispilocarpic acid esters, processes for the preparation of the said novel compounds, pharmaceutical compositions containing the novel compounds and their use.

BACKGROUND OF THE INVENTION (+)-pilocarpine, (3S-cis)-3-ethyldihydro-4-[(1-methyl-1H -imidazol-5-yl)methyl]-2(3H)-furanone, is a drug which is used for the treatment of glaucoma, which lowers the ocular pressure by increasing the flow of chamber fluid from the eye. The intraocular pressure reducing effect of pilocarpine is based on the ciliary muscle contracting effect of the drug widening the angle of the anterior chamber which is important from the viewpoint of the outflow of the chamber fluid and the outflow of the fluid is facilitated.

The reduction of the intraocular pressure is, however, not the only effect of pilocarpine in the eye. When the drug concentration is sufficiently high, the contracting effect of pilocarpine on the ciliary muscle is increased, resulting in the adaptation of the ocular lens for seeing at close distance. It is then difficult for the patient to accommodate the eye for seeing at a greater distance, which is inconvenient for the patient. Pilocarpine also causes the iris of the eye to contract, the pupil of the eye decreasing considerably. Besides these effects on the eye which are unnecessary from a medical point of view and unpleasant for the patient, pilocarpine may cause side effects outside the eye. Such effects are i.a. increased salivation and bradycardia. Conventionally glaucoma patients administer pilocarpine locally as eyedrops. Administered in such a manner, however, only about 1% of the pilocarpine dose is absorbed by the eye and about 70% in the blood stream. The low absorption rate of pilocarpine in the eye is due to three major factors:

1) the drop is quickly flushed away from the surface of the eye
2) the rapid absorbance of pilocarpine into the blood stream through the conjunctiva of the inner surface of the eyelid
3) the poor corneal penetration capability of pilocarpine.

Pilocarpine is absorbed into the eye through the cornea. In the cornea it is first absorbed in the dense epithelium layer on the eye surface containing cell membrane lipids (fats) in abundance. However, pilocarpine is not very fat soluble wherefore it penetrates relatively little into the corneal epithelium. The corneal epithelium functions simultaneously as a film restricting the absorption of pilocarpine, and as a storage, which delivers pilocarpine through the aqueous stroma and endothelium of the cornea into the fluid of the anterior chamber. From the chamber fluid pilocarpine has easy access to its action site, the ciliary muscle. The duration of the effect of pilocarpine in the eye is substantially reduced by its partial conversion to inactive pilocarpic acid and the rapid departure of pilocarpine from the eye through the chamber fluid circulation and the blood circulation of the iris.

The low absorption into the inner parts of the eye and the short duration of action of pilocarpine administered into the eye cause difficulties in drug treatment. In order to improve the action of the drug and increase its duration of action, pilocarpine must be used in relatively big doses. From this follows that high pilocarpine levels are obtained in the chamber fluid, in the iris and the ciliary muscle which lead to a strong contraction of the pupil and adaptation of the eye to seeing at close distance. Increasing the dose of pilocarpine is, in addition, a relatively ineffective way of prolonging the action of the drug, the drug being of the type that is rapidly excreted from the eye, and thus pilocarpine eyedrops are administered 3 to 8 times daily depending on the patient. Administration of eyedrops so frequently is inconvenient from the point of view of the patient, especially when the administration of the drops is always followed by side effects in the eye. The use of big doses also increase the amount of pilocarpine absorbed in the blood circulation and thus also the risk for other side effects.

Efforts have been aimed at solving the afore said disadvantages relating to the poor absorption of pilocarpine by using pilocarpine prodrug derivatives which absorb better into the corneal epithelium. Such derivatives have to be more fat soluble than pilocarpine in order to improve absorption. In addition, they have to degrade as completely as possible in the corneal epithelium to liberate the pharmaceutically effective pilocarpine and the ineffective pro-moiety. The degree of degradation in the cornea is dependant on the residence time of the derivative in the corneal epithelium and its degradation rate therein. The residence time of the derivative in the epithelium is increased with increased lipophilicity and decreased diffusion coefficient.

Up to now two kinds of prodrug derivatives of pilocarpine have been developed. Bodor discloses in the U.S. Pat. No. 4,061,722 pilocarpine prodrugs based on quaternary ammonium compounds. Bundgaard et al. have disclosed in EP-patent application 0 106 541 pilocarpic acid diesters, by means of which improved ocular absorption has been reached. The said pilocarpic diesters are, however, associated with certain disadvantages, such as poor aqueous solubility and eye irritation. Also, a great number of undesirable side products are released from the diesters as compared to the active agent itself, pilocarpine.

The present invention relates to novel bispilocarpic acid esters, i.e. bispilocarpates, by means of which the aforementioned disadvantages may largely be eliminated or at least minimized. Thus the prodrug derivatives according to the invention degrade at least as rapidly to pilocarpine and the pro-moiety when compared to the prodrugs of Bundgaard et al. of corresponding lipophilicity, and they also promote at least to the same degree the penetration of pilocarpine through the cornea. In addition, the bispilocarpate derivatives carry into the cornea one pro-moiety for every two pilocarpine molecules, whereas the derivatives of Bundgaard et. al carry one pro-moiety for every pilocarpine molecule. The diffusion coefficients of the bispilocarpate derivatives in the corneal epithelium is smaller than those of the Bundgaard compounds, wherefore still undegraded bispilocarpate derivatives remain in the corneal epithelium longer. Thus there will be more time left for the prodrug to break down completely. In addition, the novel compounds of the invention have a better solubility, and are thus better suited for the preparation of drug formulations.

Thus the invention allows for extended slow drug release from the cornea into the inner parts of the eye, by means of which it is possible to effectively prolong the duration of action of pilocarpine and also reduce the peaks of high pilocarpine concentration in the eye, which is of importance from the view of reducing the afore mentioned side effects.

SUMMARY OF THE INVENTION

The novel pilocarpine prodrug-derivatives, specifically bispilocarpic acid esters, that is bispilocarpates of the present inventions, have the general formula I

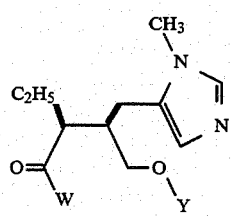

wherein
A) Y is hydrogen or

wherein R is hydrogen, $C_1$–$C_{18}$-alkyl, $C_2$–$C_{18}$-alkenyl, $C_2$–$C_{18}$-alkynyl, optionally substituted $C_3$–$C_7$-cycloalkyl or $C_3$–$C_7$-cycloalkenyl, optionally substituted aryl or aryl lower alkyl, and W is the group

—O—A—O—Z—Y' wherein Y' has the meaning of hydrogen or the group

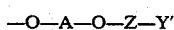

R', wherein R' has the meaning of R above, whereby R' can be the same as or different from R, A is optionally hydroxy or protected-hydroxy substituted $C_1$–$C_{18}$-alkylene, $C_2$–$C_{18}$-alkenylene, $C_2$–$C_{18}$-alkynylene, which may be substituted by optionally substituted $C_3$–$C_7$-cycloalkyl, $C_3$–$C_7$-cycloalkenyl, aryl, or aryl lower alkyl, or A is optionally substituted $C_3$–$C_7$-cycloalkylene or $C_3$–$C_7$-cycloalkenylene or arylene, or A is the aforementioned alkylene, alkenylene, or alkynylene, which as a chain member contains the afore defined cycloalkylene, cycloalkenylene or arylene group, and —Z—Y' is

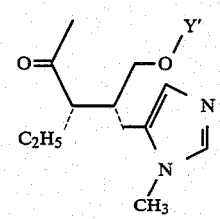

or
B) W is —OR, wherein R has the meaning given above, Y is

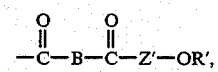

wherein R' has the meaning given above and B has the meaning given for A above, and —Z'—OR' is

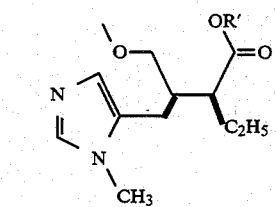

or
C) W and Y mean together (—W—Y—)

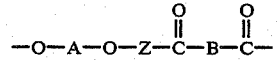

wherein A and B have the meaning given above and Z has the same meaning as in the group —Z—Y' above, as well as the acid addition salts of the said compounds.

DETAILED DESCRIPTION OF THE INVENTION

In connection with the afore mentioned general formula I, $C_1$–$C_{18}$-alkyl is straight or branched, advantageously lower alkyl with 1–10 C-atoms, preferably 1–4 C-atoms, such as methyl, ethyl, propyl, isopropyl or butyl, isobutyl, sec-butyl or tert-butyl, or pentyl, hexyl, heptyl, octyl, nonyl and decyl.

$C_2$–$C_{18}$-alkenyl may be straight or branched and is advantageously lower alkenyl with 2–10 C-atoms, preferably 2–4 C-atoms and means ethenyl, 1-methylethenyl, 1-propenyl, allyl or 1-, 2- or 3-butenyl, 2-methyl-2-propenyl or also 1-, 2-, 3- or 4-pentenyl, iso-pentenyl, 3-methyl-2-butenyl, hexenyl, heptenyl, octenyl, nonenyl or decenyl. The said alkenyls may be either in E-or Z-form, or may be conjugated or non-conjugated dienyls, such as 3,7-dimethyl-2,6-octadiene, trienyls, such as farnesyl, or polyenyls.

$C_2$–$C_{18}$-alkynyl may be straight or branched and is advantageously lower alkynyl with 2–10 C-atoms, preferably 2–4 C-atoms, and means for example ethynyl, 1-propynyl, propargyl or butynyl, or also pentynyl, hexynyl, heptynyl, octynyl, nonynyl or decynyl. Also conjugated or nonconjugated di-, tri- and poly-ynyls and alkenynyls come into question.

Cycloalkyl and -alkenyl, and cycloalkylene and -alkenylene, respectively, contain 3–7 C-atoms, preferably 3-6 C-atoms and may be unsubstituted or substituted with lower alkyl, wherein lower alkyl preferably contains 1-4 C-atoms.

Aryl means a substituted or unsubstituted carbocyclic aromatic ring, such as phenyl, or a bicyclic unsaturated or partly saturated ring system, such as for example naphtyl, indenyl, indanyl, tetrahydronaphtyl or biphenyl, etc. As substituents lower alkyl, lower alkoxy, nitro or halogen come into question, whereby lower alkyl and lower alkoxy preferably contain 1-4 C-atoms.

Monocyclic aryl and aralkyl may be illustrated with the formula

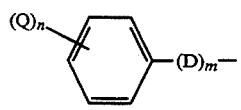

wherein the groups Q independently have the meaning of $C_1$-$C_4$-alkyl, $C_1$-$C_4$-alkoxy, halogen or nitro, n is an integer 0-3, m is an integer 0 or 1, and D means a straight or branched $C_1$-$C_6$-alkylene or conjugated or non-conjugated $C_2$-$C_6$-alkenylene or -alkynylene. Halogen is chlorine, bromine, fluorine or iodine.

A means as a bivalent alkylene, alkenylene, or alkynylene group such a straight or branched bivalent group which contains 1-18 or 2-18 C-atoms, respectively, preferably however 1-10 and 2-10 C-atoms, respectively, such as methylene, ethylene, propylene, butylene, but also pentylene, hexylene, heptylene, octylene, nonylene, and decylene, and corresponding unsaturated bivalent groups, which as a chain substituent may contain the afore defined cycloalkyl, cycloalkenyl, aryl or aralkyl group, or which may be substituted by hydroxy or protected-hydroxy. Protected hydroxy is the group -OR" or —OCOR", wherein R" means $C_1$-$C_4$-alkyl, $C_3$-$C_6$-cycloalkyl, aryl or aryl-$C_1$-$C_4$-alkyl, wherein aryl has the meaning given above.

A may as cycloalkylene and cycloalkenylene, respectively, mean for example cyclopropylene, cyclobutylene, cyclopentylene, cyclohexylene, or cycloheptylene, and the corresponding unsaturated groups. The last mentioned bivalent ring systems may also form part of the said alkylene, alkenylene and alkynylene groups.

Arylene as such or as a member of a chain may be illustrated with the following formula

wherein the bivalent Ar has the meaning of the above defined optionally substituted aryl group, D and D' are the same and different and have the meaning of D above, especially, methylene or ethylene, and m and m' are independently integers 0 or 1. Arylene is preferably phenylene or naphtylene.

Acid addition salts of the compounds of the formula I are preferably pharmaceutically acceptable addition salts with non-toxic inorganic or organic acids. As examples of suitable acids hydrochloric, hydrobromic, sulphuric, nitric, phosphoric acid etc., and as organic acids for example, acetic, propionic, stearic, oxalic, malonic, succinic, glutaric, adipic, maleic, fumaric, malic, tartaric, citric, ascorbic, benzoic, pamoic or sulphonic acid, such as mesyl or tosyl acid, may be mentioned.

The compounds of the invention are thus dimeric ester derivatives of pilocarpic acid, i.e. bispilocarpates, of which there are three major types in accordance with the subgroups A) to C) mentioned in connection with the general formula above. Thus the bispilocarpates of the subgroup A) may be illustrated with the formula I'

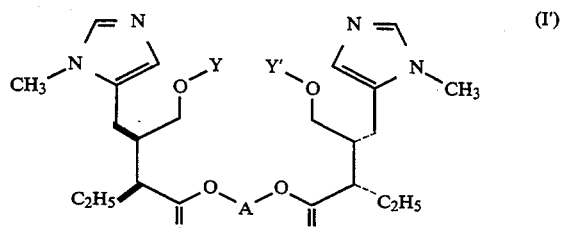

The bispilocarpates of the subgroup B) may be illustrated with the formula I"

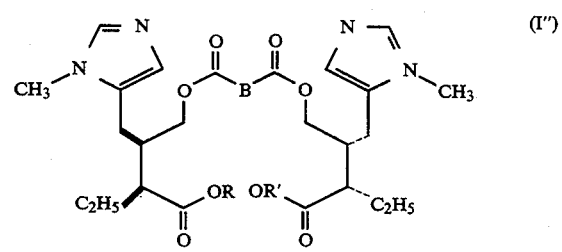

The bispilocarpate macrolides in accordance with the subgroup C) may be illustrated with the formula I'''

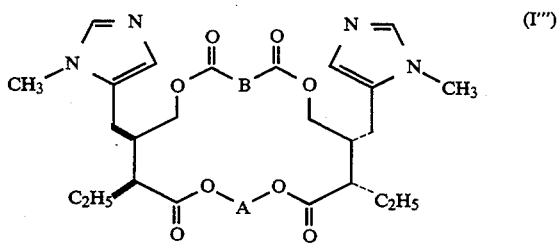

In the aforementioned formulas I', I" and I''' the symbols have the meanings given in connection with the formula I.

In the compounds I, both groups R and R', respectively, preferably are the same.

Preferred compounds are e.g. the bispilocarpates according to the formula I' wherein Y and Y' are hydrogen and then specifically O,O'-dihydrogen (1,4-, 1,3-, 1,2-xylylene)-, especially O,O'-dihydrogen (1,4-xylylene)-, and -(1,3-propylene)-, -(1,5-pentylene)-, -(1,6-hexylene) bispilocarpate and -(1,7-heptylene) bispilocarpate.

Preferred diacyl bispilocarpates of the formula (I') are e.g. O,O'-diacetyl-, O,O'-dipropionyl-, O,O'-dibutyryl-, O,O'-divaleryl-, O,O'-dibenzoyl- and O,O'-dicyclopropylcarbonyl (1,4-xylylene)—, (1,5-pentylene)— and (1,6-carbonyl hexylene) bispilocarpate.

Of these may especially be mentioned: O,O'-dipropionyl (1,4-xylylene) bispilocarpate O,O'-dicyclopropylcarbonyl (1,4-xylylene) bispilocarpate O,O'-dicyclopropylcarbonyl (1,6-hexylene) bispilocarpate.

Another preferred subgroup of the compounds of the formula (I') is formed by the compounds wherein Y is —C(=O)—R, and R is $C_1$-$C_4$-alkyl, $C_3$-$C_6$-cycloalkyl, benzyl or phenyl, and A is 1,2-ethylene, 1,3-propylene or 1,4-butylene, optionally substituted with hydroxy, the group Y—O—, Y having the meaning given above, or with one or two methyl groups.

Within this subgroup, compounds are preferred wherein Y is —C(=O)—R and R is $C_1$–$C_4$-alkyl, $C_3$–$C_6$-cycloalkyl or phenyl, and A is ethylene, or A is 1,3-propylene, which can be substituted in its 2-position with hydroxy, the group Y—O— wherein Y has the meaning given, or with one or two methyl groups.

Specifically, the following compounds may be mentioned: O,O'-dicyclopropylcarbonyl (1,2-ethylene) bispilocarpate O,O'-dicyclobutylcarbonyl (1,2-ethylene) bispilocarpate O,O'-dicyclopropylcarbonyl (1,3-propylene) bispilocarpate O,O'-dicyclobutylcarbonyl (1,3-propylene) bispilocarpate O,O'-dicyclopropylcarbonyl (2-methyl-1,3-propylene) bispilocarpate O,O'-dicyclopropylcarbonyl (2,2-dimethyl-1,3-propylene) bispilocarpate O,O'-dipropionyl (1,3-propylene) bispilocarpate O,O'-dicyclopropylcarbonyl (2-hydroxy-1,3-propylene) bispilocarpate O,O'-dicyclopropylcarbonyl (2-cyclopropylcarbonyloxy-1,3propylene) bispilocarpate O,O'-dipivalyl (1,2-ethylene) bispilocarpate O,O'-dipivalyl (1,3-propylene) bispilocarpate O,O'-di(1-methylcyclopropylcarbonyl) (1,2-ethylene) bispilocarpate O,O'-dicyclopentylcarbonyl (1,2-ethylene) bispilocarpate O,O'-dipropionyl (1,2-ethylene) bispilocarpate O,O'-diisobutyryl (1,2-ethylene) bispilocarpate O,O'-dipropionyl (2-hydroxy-1,3-propylene) bispilocarpate O,O'-dicyclohexylcarbonyl (1,2-ethylene) bispilocarpate O,O'-dicyclopentylcarbonyl (1,3-propylene) bispilocarpate O,O'-dicyclohexylcarbonyl (1,3-propylene) bispilocarpate O,O'-dibenzoyl (1,2-ethylene) bispilocarpate O,O'-dibenzoyl (1,2-propylene) bispilocarpate.

One preferred subgroup of the compounds of the formula (I'') is formed by the compounds, wherein W is OR', wherein R' has the meaning of $C_1$–$C_4$-alkyl, $C_3$–$C_6$-cycloalkyl, benzyl or phenyl, and B is 1,2-ethylene, 1,3-propylene or 1,4-butylene, optionally substituted with hydroxy, the group Y—O—, Y having the meaning given above, or with one or two methyl groups. Within this group, preferred are the compounds wherein R' has the meaning of $C_1$–$C_4$-alkyl or $C_3$–$C_6$-cycloalkyl, and B is 1,2-ethylene, 1,3-propylene or 1,4-butylene.

Another preferred group of compounds of the formula I'' is comprised of e.g. the (dibenzyl) bispilocarpates, such as O,O'-glutaryl (dibenzyl) bispilocarpate.

Reference is especially made to the following compounds: O,O'-succinyl (diethyl) bispilocarpate O,O'-succinyl (diisopropyl) bispilocarpate O,O'-succinyl (di-t-butyl) bispilocarpate O,O'-succinyl (dicyclopropyl) bispilocarpate O,O'-succinyl (dicyclobutyl) bispilocarpate O,O'-glutaryl (diisopropyl) bispilocarpate O,O'-glutaryl (di-t-butyl) bispilocarpate O,O'-glutaryl (dicyclopropyl) bispilocarpate O,O'-glutaryl (dicyclobutyl) bispilocarpate.

The invention relates also to a process for the preparation of the compounds according to the formula I.

According to the process of the invention a) for the preparation of a compound of the formula (I') defined above, pilocarpic acid of the formula

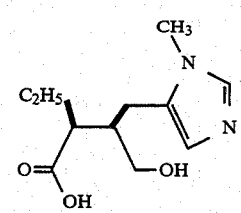

or its salt is reacted with a compound of the formula X—A—X', wherein X and X' are independently hydroxy, or a leaving group, such as halogen, acyloxy, or alkyl or aryl sulfonyloxy, for the preparation of a compound of the formula (II)

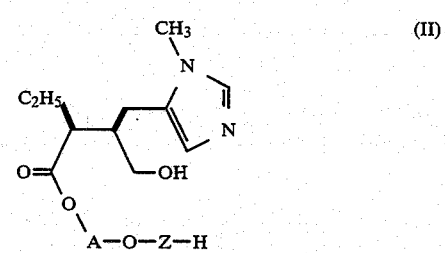

(II)

wherein A and Z have the meanings indicated before, which, if desired, is converted to a compound of the formula I', wherein Y is different from hydrogen, by reacting the same with an acid of the formula $RCO_2H$, and when R is different from R', thereafter with an acid of the formula $R'CO_2H$, or with a functional derivative of these acids, and optionally the compound of the formula (I') is converted to its acid addition salt, or b) for the preparation of a compound of the formula (I'') as defined above, a compound of the formula (III) or (III') respectively

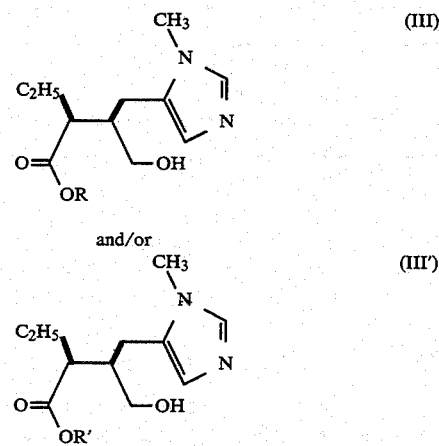

(III)

and/or (III')

wherein R and R' have the meaning given above, is reacted with a dicarboxylic acid of the formula (IV)

(IV)

wherein B has the meaning given above, or with a bifunctional acid derivative thereof, and optionally the compound obtained with the formula (I'') is converted to its acid addition salt, or c) for the preparation of a compound of the formula (I''') as defined above, a compound of the formula

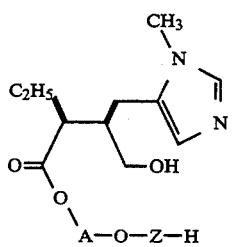

wherein A and Z have the meanings given above, is reacted with a dicarboxylic acid of the formula (IV)

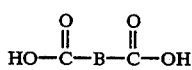

wherein B has the meaning given above, or with a bifunctional acid derivative thereof, and optionally the obtained compound with the formula (I''') is converted to its acid addition salt.

For the preparation of the compound used above as starting material in the process b), pilocarpic acid as defined above, is reacted with a compound of the formula RX and/or R'X, wherein X has the meaning of hydroxy, or a leaving group, such as halogen, acyloxy, or alkyl- or aryl sulfonyloxy, and R and R' have the same meaning as above.

In the above mentioned reactions, as the functional acid derivatives preferably the halogenides, anhydrides, alkyl and aryl sulfonates thereof are used. As the reaction medium, solvents such as hydrocarbons, halogenated hydrocarbons, ethers, ketones etc are used, which are inert to the reagents. Suitable hydrocarbons are the aromatic hydrocarbons, such as benzene and alkyl benzenes, such as toluene and xylene. Suitable halogenated hydrocarbons are for example dichloromethane, chloroform and chlorobenzene. As ketones acetone, ethyl methyl ketone and isobutyl methyl ketone may be mentioned, and as ethers diethyl ether, di-, isopropyl ether, dibutyl ether and 1,4-dioxane may be mentioned. Other suitable solvents include dimethyl sulfoxide, dimethylformamide and acetonitril.

The reaction temperature is not critical but may vary for example from −10° C. to the boiling point of the solvent. Suitably room temperature is used. The reaction time may vary with broad limits and is conventionally 12–72 hours, usually about 24 hours. It is suitable to use acid binding agents in the reactions, such as alkali metal and alkaline earth metal carbonates or organic bases. Suitable metal carbonates include sodium carbonate and potassium carbonate and as organic bases pyridine and its homologues, 4-(dimethylamino)pyridine, quinoline and its homologues, N,N-dimethylaniline and trialkylamines, especially triethyl amine. The said reactions may take place either in a homogenous solution or in a heterogenic system, such as under PTC-conditions.

The ester bonds of the compounds according to the invention may be formed also by using known water cleaving reagents, such as carbodiimides. In some cases also the known acid catalyzed esterification reactions may come into question.

The pharmaceutical compositions according to the invention are made in a known manner by using vehicles and other adjuvants known in the art. The vehicles may, for example, be liquids, suspensions or emulsions, or creams and ointments. The composition may also be formed into a solid pharmaceutical form to be inserted in the eye. A suitable form of administration is for example an eyedrop solution which contains the compound according to the invention at a suitable concentration, for example 0.1 to 4%, in a sterile aqueous solution buffered to a suitable pH or adjusted to a suitable pH with an acid or a base, the compound preferably being used in its water soluble acid addition salt form. An eyedrop solution with the said desired concentration is administered into the eye, depending on the patient, preferably 1 to 3 times a day.

TEST REPORT

TEST METHODS

The compounds of the invention have been tested in the following tests. Pilocarpine diesters known from the EP patent application EP-0 106 541 have been tested in the corresponding tests under the same conditions and compared to a representative number of the bispilocarpates according to the invention, specifically those disclosed in Examples 1–21.

1) Stability of the compounds

The stability of the test compounds were tested with buffer hydrolyses. The ionic strength ($\mu$) of the buffers was 0.5, the pH-values used 4.2, 6.0, 7.4 and 9.0 and the temperatures used 37° C., 50° C., 60° C. and 70° C.

The half-times $T_{\frac{1}{2}}$ calculated on basis of the degradation constant k obtained for each studied compound ($T_{\frac{1}{2}}=0.693/k$; $k=2.303 \times kk$, wherein kk is the angular coefficient of the plot which illustrates the logarithm of the remaining ester as a function of time) in a buffer solution of said pH, are indicated in the Table I below, which values refer to half-times at 37° C.

The results in the Table I indicate that the bispilocarpates according to the invention are more stable in an acidic solution than in a basic, and at least as stable as the diesters according to the EP-patent application 0 106 541.

The storage stability of the derivatives under different storage conditions may be estimated by determining the degradation constants at different temperatures and calculating the degradation constant k at the desired temperature from the equation of the plot corresponding to the Arrhenius equation (1), wherein log k is given as a function of [1/T].

$$\text{Log } k = \text{Log } A - \frac{E_a}{2.303R} \times \frac{1}{T} \quad (1)$$

From the degradation constant (k) obtained at the desired temperature the shelf-life-time $t_{10\%}$ ($t_{10\%}=0.104/k$) which indicates the time during which 10% of the drug has degraded may be calculated. By way of example it may be mentioned that the $t_{10\%}$-time of O,O'-dipropionyl (1,4-xylylene) bispilocarpate at 4° C. is almost 500 days.

2) Lipophilicity

The lipophilicity of the compounds were studied by determining the partition coefficients (P) of the compounds at a pH of 7.40. The measurements were made either in an octanol-buffer mixture by determining the concentration of the compound to be studied in the buffer phase by HPLC. The partition coefficients of the very lipophilic compounds were, however, determined by reverse phase (RP) liquid chromatography (HPLC) from the retention time (Beckmann 116 pump and 166 UV detector; Marathon autom. sample feeder).

The log P values and capacity factors k' of the compounds studied, pilocarpine and the bispilocarpates according to the invention, at 22° C. are given in the Table I below. From the results it can be seen that the compounds of the invention are considerably more lipophilic than the pilocarpine.

3) Enzyme hydrolysis

The half-times of enzyme hydrolysis of the novel bispilocarpates according to the invention and of known pilocarpic acid diesters were determined in a plasma/buffer pH 7.4-mixture (80%-20%) at 37° C. The degradation constants (k) for the compounds tested and determined from the plot showing the logarithm of remaining diester as a function of time and the half-lives $T_{\frac{1}{2}}$ are shown in Table II below.

From the results it may be seen that in buffer solutions the stable test compound degrades under the influence of an enzyme (esterase) to a O,O'-dihydrogen bispilocarpate intermediate, which spontaneously degrades at pH 7.40 to pilocarpine. Consequently the effect of the bispilocarpate intermediate on the rate of formation of pilocarpine is very significant. The formation of pilocarpine was almost complete irrespective of the epimerization possibility of the intermediate. The amount of isopilocarpine formed varied from 0 to 10%, as also the pilocarpine formed epimerized, if the duration of hydrolysis was very long.

4) Corneal permeability

The corneal permeability of pilocarpine hydrochloride and its most promising prodrug derivatives as evaluated from the tests described above were studied in a diffusion chamber, wherein the migration of the compound from the delivering phase (epithelium side) through the cornea to the acceptor side (endothelium side) of the diffusion chamber. In the study, rabbit eye cornea was used.

From the samples taken from the acceptor side of the diffusion chamber, both the concentration of the prodrug and the liberated drug were determined in the acceptor phase with HPLC. Thus the rate of degradation of the prodrug in the cornea was determined.

The permeability coefficients ($P_{app}$, cm/s) calculated from the permeability rate (mmol/min), their average deviations (RSD) and the number of tests, are given in Table II below.

From the results it can be seen that with the compounds from both groups it is possible to substantially improve the permeability of pilocarpine. The results also show that the pilocarpine esters degrade in the cornea forming pilocarpine and that with the groups attached to pilocarpic acid it is possible to regulate the corneal permeability of the prodrug and the rate of formation of pilocarpine.

TABLE I

| Compound | Half-times in buffers at 37° C. | | | | Partition coefficient log P | Capacity factor (22° C.) k' |
|---|---|---|---|---|---|---|
| | pH 4.20 | 6.00 | 7.40 | 9.00 | | |
| Pilocarpine | | | | | 0.0117[1] | 0.4051 |
| Compounds from EP 106541 | | | | | | |

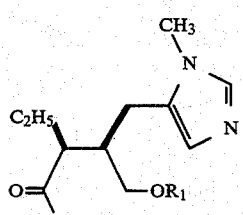

| $R_1$ | $R_2$ | $T_{\frac{1}{2}}$ (h) | | | | | |
|---|---|---|---|---|---|---|---|
| acetyl | benzyl | 7668 | 3466 | 547 | 79 | | |
| propionyl | benzyl | 2179 | 5335 | 748 | 94 | | |
| valeryl | benzyl | 8537 | — | 1169 | 303 | | |
| benzoyl | benzyl | 10667 | 4871 | 2043 | 111 | | |
| acetyl | cyclohexylmethyl | 2195 | 1663 | 503 | 73 | | |
| propionyl | cyclohexylmethyl | — | 1507 | 829 | 154 | | |
| Compound according to the invention: | | $T_{\frac{1}{2}}$ (min) | | | | | |
| Example 1 | | 2256 | 137 | 18 | 1.9 | 2.1753[1] | 0.8101 |
| Example 2 | | 2930 | 167 | 19 | 1.1 | 1.9901[1] | 0.8291 |
| Example 3 | | 1210 | 201 | 25 | 1.4 | 2.0252[1] | 0.8291 |
| Example 4 | | 4909 | 1792 | 201 | 18 | 2.6743[1] | 1.1266 |
| Example 5 | | 3759 | 1509 | 150 | 14 | 1.8360[1] | 0.8924 |
| Example 6 | | 4378 | 1474 | 125 | 14 | 1.5714[1] | 0.7532 |
| Example 7 | | 7206 | 1136 | 158 | 10 | 1.1627[1] | 0.6582 |
| Example 8 | | 4040 | 618 | 72 | 4 | 0.6830[1] | 0.6139 |
| | | $T_{\frac{1}{2}}$ (h) | | | | | |
| Example 9 | | 3964 | 1161 | 274 | 34 | 3.0432[1] | 1.3987 |
| Example 10 | | 2203 | 1214 | 400 | 47 | 4.0843[1] | 2.3038 |
| Example 11 | | 5993 | 1114 | 177 | 137 | 5.5604[2] | 4.0127 |
| Example 12 | | | | | 7 | 7.0165[2] | 7.3861 |
| Example 13 | | 63323 | 8445 | 3545 | 339 | 4.2015[1] | 2.4684 |
| Example 14 | | | | | 8 | 6.4929[2] | 5.9304 |
| Example 17 | | 4761 | 2546 | 251 | 28 | 5.2038[2] | 3.4557 |
| Example 16 | | 4187 | 2198 | 757 | 43 | 5.4093[2] | 3.7658 |

TABLE I-continued

|  | Half-times in buffers at 37° C. | | | | Partition coefficient | Capacity factor (22° C.) |
| --- | --- | --- | --- | --- | --- | --- |
| Compound | pH 4.20 | 6.00 | 7.40 | 9.00 | log P | k' |
| Example 15 | 3141 | 1647 | 655 | 70 | 5.8242[1] | 4.4810 |
| Example 18 | 834 | 49 | 6 | 0.4 | 5.7137[1] | 4.2785 |
| Example 19 | 1581 | 913 | 55 | 38 | 7.0000[1] | 7.3354 |
| Example 20 | 3221 | 3405 | 664 (at 50° C.) | | 0.800 (at pH 5.0) | |
| Example 21 | 4624 | 2368 | 553 (at 50° C.) | | 0.401 (at pH 5.0) | |

[1]partition coefficient determined with an octanol-buffer mixture
[2]Log P determined from the equation log k' = 0.182 Log P − 0.4086

TABLE II

|  | Degradation coefficient (k) and half-times ($T_{\frac{1}{2}}$) in plasma (80%), 37° C. | | $P_{app}$ | Permeability coefficient | |
| --- | --- | --- | --- | --- | --- |
|  |  |  |  | Relative standard deviation | Number of tests |
| Compound | k (min$^{-1}$) | $T_{\frac{1}{2}}$ (min) | (cm/s × 10$^{-5}$) | (RSD) | n |
| Pilocarpine |  |  | 0.41 | (22.9) | 6 |
| Compounds from EP-106541 | | | | | |
| R$_1$   R$_2$ | | | | | |
| acetyl       benzyl | 0.04353 | 16 | 1.17 | (14.0) | 6 |
| propionyl    benzyl | 0.10801 | 6 | 1.43 | (26.8) | 6 |
| valeryl      benzyl | 0.07876 | 9 | 1.15 | (26.4) | 6 |
| octanoyl     benzyl | 0.02556 | 27 |  |  |  |
| benzoyl      benzyl | 0.03800 | 18 | 0.87 | (23.8) | 5 |
| 3-chlorobenzoyl  benzyl | 0.03132 | 22 | 0.72 | (24.4) | 5 |
| acetyl       cyclohexylmethyl | 0.00967 | 72 |  |  |  |
| propionyl    cyclohexylmethyl | 0.02957 | 33 | 0.13 | (29.3) | 6 |
| valeryl      cyclohexylmethyl | 0.02487 | 28 |  |  |  |
| benzoyl      cyclohexylmethyl | 0.00599 | 116 |  |  |  |
| 3-chlorobenzoyl  cyclohexylmethyl | 0.00299 | 231 |  |  |  |
| Compound according to the invention | | | | | |
| Example 9 | 0.07370 | 9 | 0.93 | (33.2) | 6 |
| Example 10 | 0.11837 | 6 | 3.05 | (14.7) | 6 |
| Example 11 | 0.06149 | 11 | 2.15 | (34.0) | 9 |
| Example 12 | 0.05734 | 12 | 1.82 | (34.0) | 4 |
| Example 13 | 0.04998 | 14 | 1.58 | (34.1) | 4 |
| Example 14 | 0.00737 | 94 |  |  |  |
| Example 17 | 0.00368 | 188 |  |  |  |
| Example 16 | 0.05044 | 14 |  |  |  |
| Example 15 | 0.02487 | 28 |  |  |  |
| Example 18 | 0.00415 | 167 |  |  |  |
| Example 19 | 0.00322 | 215 |  |  |  |
| Example 20 |  | 15 | 0.64 |  | 4 |
| Example 21 |  | 13 | 0.61 |  | 4 |

Further tests were carried out on the compounds illustrated in Examples 22-35, the results of which are shown in Table III below.

The lipophilicity of the compounds was determined by measuring the partition coefficients (P) of the compounds at pH-values 7.40 and 5.00. The measurements were made in a 1-octanol-phosphate buffer mixture by determining the concentration of the compound to be studied in the buffer phase before and after partitioning.

The half-lives of enzyme hydrolysis of the bispilocarpates according to the invention were determined in a plasma/buffer mixture and/or rabbit corneal homogenate.

The half-lives of enzyme hydrolysis of bispilocarpic acid diesters were determined in a plasma/phosphate buffer pH 7.40 mixture (80%-20%)) at 37° C. The logarithm of remaining diester was presented as a function of time and from the plot obtained was determined the half-life $T_{\frac{1}{2}}$.

The half-lives of enzyme hydrolysis of bispilocarpic acid diesters were also determined in rabbit corneal homogenate pH 7.40 at 37° C. The corneal homogenate was prepared in 0.05M Tris buffer. The logarithm of remaining diester was presented as a function of time and from the plot obtained the half-life $T_{\frac{1}{2}}$ was determined.

The corneal penetration was studied and calculated as described above.

|  | $T_{\frac{1}{2}}$ | | Log P | | $P_{app}$ × 10$^{-6}$ |
| --- | --- | --- | --- | --- | --- |
| Example | corneal homogenate min | plasma min | pH 5.0 | pH 7.4 | cm/s |
| 22 | — | — | — | 0.50 | — |
| 23 | 26 | 33 | −0.58 | 2.83 | 2.60 |
| 24 | 9 | 3 | −0.77 | 2.57 | 1.67 |
| 25 | 4 | 6 | 0.30 | 3.76 | 10.46 |
| 26 | 7 | 5 | −0.61 | 2.93 | 3.19 |
| 27 | 14 | — | −0.30 | 3.43 | 4.26 |
| 28 | 4 | 5 | 0.60 | — | 12.86 |
| 29 | 97 | — | — | — | 6.55 |
| 30 | — | — | 1.71 | — | 10.77 |
| 32 | 26 | — | −0.46 | — | 1.17 |
| 33 | 39 | — | −0.27 | — | — |
| 34 | 14 | — | −0.02 | — | — |
| 35 | 39 | — | — | 2.49 | — |

Conclusion

The results show that the compounds of the invention are hydrolyzed in the cornea forming pilocarpine and that with the groups attached to pilocarpic acid it is possible to regulate the corneal penetration of the pro-drug and the rate of formation of pilocarpine. It is worth mentioning that the permeability coefficient is smaller for derivatives which release pilocarpine only at a slow rate, due to e.g. the appropriately slow chemical hydrolysis of the intermediate liberated from the derivative, than for derivatives, from which pilocarpine is released rapidly. The diffusion coefficient and thus the diffusion rate of the compounds of the invention is lower than that of the Bundgaard compounds, and thus more time is left for the formation of pilocarpine giving rise to a prolonged effect of the prodrug.

The fat solubility, enzymatic hydrolysis, corneal penetration and the chemical hydrolysis of the intermediate of the compounds according to the invention and thus the formation of active pilocarpine in the eye can be easily regulated according to purpose by changing the chemical groups attached to the pilocarpic acid. Bispilocarpic acid diesters are enzymatically hydrolyzed to bispilocarpic acid esters and pilocarpic acid monoesters respectively, which are chemically (spontaneously) hydrolyzed to pilocarpine.

The compounds of the invention have proven to be stable compounds also in water based solutions and they thus enable the preparation of eyedrop formulations.

When comparing the compounds according to the invention to the compounds according to the EP application 0 106 541, it is found that the compounds according to the invention are at least as good as the known compounds in all fields. A substantial advantage of the compounds according to the invention is, however, that the bispilocarpates of the invention produce two pilocarpine molecules for one bispilocarpate molecule, from which follows in turn relatively less products of metabolism split off from the prodrug-structure, especially monocarboxylic acids, alkohols, etc. per pilocarpine molecule. By minimizing the amount of products of metabolism it is possible to reduce eye drug related irritation and stinging of the eye.

As fat soluble compounds the bispilocarpic acid diesters of the invention are effectively absorbed into the corneal epithelium, where the corneal esterases rapidly release a suitable water soluble intermediate (e.g. O,O'-dihydrogen (1,2-ethylene) bispilocarpate (from IA) or 0-hydrogen (ethyl) bispilocarpate (from IB) resp.), which as a water soluble compound is capable to migrate from the epithelium to the stroma and from there into the inner parts of the eye towards its action site releasing pilocarpine continuously during migration. Thus there is no excessive accumulation of prodrug-derivative nor pilocarpine in the corneal epithelium, which might cause irritation of the eye.

By means of the compounds of the invention it is possible to eliminate to a large extent the disadvantages relating to drug treatment with pilocarpine (poor biological availability, system and eye side-effects, frequent administration and thus poor patient compliance). Due to the better corneal permeability, the compounds of the invention may be administered in considerably smaller doses and the number of doses/day may be reduced, whereby the side-effects are reduced, patient compliance is improved and the drug treatment of the glaucoma patient is made more effective.

The following examples illustrate the invention without limiting the same in any way.

Equipment Used

Melting point determination: Reichert Thermovar apparatus

Determination of refraction index: Atago Illuminator apparatus pKa-value determination: titrating the derivative in a water-ethanol mixture (50%-50%)

Mass spectrometer: VG 70-250SE
  Test conditions in the electron bomb ionisator:
  electron energy: 70 eV (unless otherwise mentioned)
  ionisation current: 500 µA
  ionisation chamber temperature: 150° C.
  sample holder temperature 30° C.→500° C. in 2-5 minutes
  resolution: 10.000

Thermospray-mass spectrometer: VG thermospray/-plasmaspray VG Trio-2 quadropole Beckmann 112 pump
  Test conditions in the thermospray-ionisation optimized daily NMR-spectrometer: Bruker AC 250/Aspect 3000
  $^1H/^{13}C$ 5 mm dual probe
  $CD_3OD$ 20 mg/ml
  δ ppm (tetramethylsilane=0)

Example 1

O,O'-Dihydrogen (1,4-xylylene) bispilocarpate (Formula I': Y=Y'=H; A=1,4-xylylene)

a) Pilocarpic acid sodium salt

Pilocarpine hydrochloride (3.92 g; 16.00 moles) was dissolved in distilled water (4 ml) and the solution was cooled to about 0° C. To the solution 18 ml of ice cold 2M NaOH were added in four portions. The solution was left standing at about 0° C. for one hour. After neutralizing excess NaOH with 5 ml of 1M HCl, the solution was evaporated under reduced pressure. The residue was dissolved in 60 ml of absolute ethanol and mixed for 10 minutes at 60° C. After cooling to 4° C. undissolved NaCl was removed by filtration. The filtrate was evaporated under reduced pressure, whereby 3.93 g of sodium pilocarpate were obtained as a white, extremely hygroscopic substance.

b) O,O'-Dihydrogen (1,4-xylylene) bispilocarpate

To a solution containing 8.00 mmoles (1987 mg) of pilocarpic acid sodium salt in 60 ml of dimethyl sulfoxide, 3.00 mmoles of α,α'-dichloro-p-xylene (524 mg) in dimethyl sulfoxide were added dropwise during about one hour. The solution was mixed at room temperature for 48-72 hours and poured into 100 ml of distilled water. The mixture was extracted with two portions of each 100 ml of chloroform. The combined chloroform extracts were washed with 100 ml of distilled water, with 100 ml of 2% sodium bicarbonate solution and with 100 ml of distilled water. The chloroform extracts were dried on magnesium sulfate and the chloroform evaporated under reduced pressure, and the bispilocarpate obtained was crystallized from a chloroform/petroleum ether mixture, whereby 770 mg (1.39 mmoles) of the title compound were obtained.

M.p. 170°-171° C. $pK_a=6.25$ k'=0.8101 HR-MS-spectrum: m/e (relative intensity): no [M+·]-peak, 208 (19%), 207 (6%), 96 (42%), 95 (100%). HPLC-MS (thermospray):m/e (relative intensity): 555 [M+1] (12%), 417 (3%), 384 (4%), 347 (46%), 267 (10%), 250 (5%), 209 ( 100%). NMR: δ 7.47 bs 2H, 7.39 s 4H, 6.69 bs 2H, 5.09 s 4H, 3.51 m 4H, 3.48 s 6H, 2.65 m 2H, 2.53 m 2H, 2.42 m 2H, 1.97 m 2H, 1.67 m 4H and 0.84 t 6H.

Example 2

O,O'-Dihydrogen (1,3-xylylene) bispilocarpate (Formula I': Y=Y'=H; A=1,3-xylylene)

The compound was prepared from the sodium salt of pilocarpine (1287 mg; 5.18 mmoles) and α,α'-dibromo-m-xylene (342 mg; 1.30 mmoles) with the method disclosed in Example 1. The bispilocarpate obtained was crystallized from a ethylacetate/ether mixture. The yield was 380 mg (0.69 mmoles).

M.p. 116°–117° C. $pK_a$=6.30 k'=0.8291 HR-MS-spectrum: m/e (relative intensity): no [M+·]-peak, 209 (11%), 208 (38%), 96 (44%), 95 (100%). HPLC-MS (thermospray): m/e (relative intensity): 555 [M+1] (7%), 417 (7%), 385 (8%), 347 (46%), 267 (9%), 250 (10%), 209 (100%). NMR: δ 7.47 bs 2H, 7.44 bs 1H, 7.35 m 3H, 6.70 bs 2H, 5.09 bs 4H, 3.52 m 4H, 3.48 s 6H, 2.66 m 2H, 2.52 m 2H, 2.43 m 2H, 1.97 m 2H, 1.67 m 4H and 0.85 t 6H.

Example 3

O,O'-Dihydrogen (1,2-xylylene) bispilocarpate (Formula I': Y=Y'=H; A=1,2-xylylene)

The compound was prepared from the sodium salt of pilocarpine (1166 mg; 4.70 mmoles) and α,α'-dibromo-o-xylene (310 mg; 1.18 mmoles) with the method disclosed in Example 1. The bispilocarpate obtained was crystallized from a ethylacetate/petroleum ether mixture. The yield was 380 mg (0.69 mmoles).

M.p. 62°–64° C. $pK_a$=6.30 k'=0.8291 HR-MS-spectrum: m/e (relative intensity): no [M+·]-peak, 208 (12%), 96 (19%), 95 (100%). HPLC-MS (thermospray):m/e (relative intensity): 555 [M+1] (11%), 417 (7%), 385 (8%), 347 (46%), 267 (9%), 250 (14%), 209 (100%). NMR: δ 7.47 bs 2H, 7.34 m 4H, 6.70 bs 2H, 5.24 s 4H, 3.52 m 4H, 3.48 s 6H, 2.66 m 2H, 2.53 m 2H, 2.42 m 2H, 1.97 m 2H, 1.67 m 4H and 0.85 t 6H.

Example 4

O,O'-Dihydrogen (1,7-heptylene) bispilocarpate (Formula I': Y=Y'=H; A=1,7-heptylene)

The compound was prepared from the sodium salt of pilocarpine (1994 mg; 8.03 mmoles) and 1,7-dibromoheptane (518 mg; 2.01 mmoles) with the method disclosed in Example 1. The bispilocarpate obtained was crystallized from a chloroform/petroleum ether mixture. The yield was 1050 mg (1.91 mmoles).

M.p. 117°–120° C. $pK_a$=6.30 k'=1.1266 HR-MS-spectrum: m/e (relative intensity): 208 (16%), 96 (2%), 95 (100%). HPLC-MS (thermospray): m/e (relative intensity): 549 [M+1] (4%), 341 (16%), 267 (7%), 250 (5%), 209 (100%). NMR: δ 7.50 bs 2H, 6.73 bs 2H, 4.05 t 4H, 3.59 s 6H, 3.53 m 4H, 2.72 m 2H, 2.50 m 2H, 2.47 m 2H, 1.99 m 2H, 1.68 m 4H, 1.64 bm 8H, 1.37 m 2H and 0.88 t 6H.

Example 5

O,O'-Dihydrogen (1,6-hexylene) bispilocarpate (Formula I': Y=Y'=H; A=1,6-hexylene)

The compound was prepared from the sodium salt of pilocarpine (1353 mg; 5.45 mmoles) and 1,6-dibromohexane (499 mg; 2.04 mmoles) with the method disclosed in Example 1. The bispilocarpate obtained was crystallized from a chloroform/petroleum ether mixture. The yield was 717 mg (1.34 mmoles).

M.p. 115°–118° C. $pK_a$=6.30 k'=0.8924 HR-MS-spectrum: m/e (relative intensity): no [M+·]-peak, 208 (16%), 96 (24%), 95 (100%). HPLC-MS (thermospray): m/e (relative intensity): 535 [M+1] (5%), 327 (26%), 267 (13%), 250 (7%), 209 (100%). NMR: δ 7.49 bs 2H, 6.73 bs 2H, 4.05 t 4H, 3.60 s 6H, 3.53 m 4H, 2.72 m 2H, 2.51 m 2H, 2.47 m 2H, 1.99 m 2H, 1.67 m 4H, 1.65 m 4H, 1.41 m 4H and 0.88 t 6H.

Example 6

O,O'-Dihydrogen (1,5-pentylene) bispilocarpate (Formula I': Y=Y'=H; A=1,5-pentylene)

The compound was prepared from the sodium salt of pilocarpine (1051 mg; 4.23 mmoles) and 1,5-dibromopentane (244 mg; 1.06 mmoles) with the method disclosed in Example 1. The bispilocarpate obtained was crystallized from a ethyl acetate/petroleum ether mixture. The yield was 395 mg (0.75 mmoles).

M.p. 84°–87° C. $pK_a$=6.30 k'=0.7532 HR-MS-spectrum: m/e (relative intensity): 209 (8%), 208 (9%), 96 (27%), 95 (100%). HPLC-MS (thermospray): m/e (relative intensity): 521 [M+1] (15%), 417 (6%), 351 (9%), 313 (73%), 267 (11%), 250 (12%), 209 (100%). NMR: δ 7.50 bs 2H, 6.73 bs 2H, 4.07 t 4H, 3.60 s 6H, 3.55 m 4H, 2.73 m 2H, 2.52 m 2H, 2.48 m 2H, 1.99 m 2H, 1.68 m 4H, 1.64 m 4H, 1.52 m 2H and 0.89 t 6H.

Example 7

O,O'-Dihydrogen (1,4-butylene) bispilocarpate (Formula I': Y=Y'=H; A=1,4-butylene)

The compound was prepared from the sodium salt of pilocarpine (1069 mg; 4.31 mmoles) and 1,4-dibromobutane (233 mg; 1.08 mmoles) with the method disclosed in Example 1. The bispilocarpate obtained was crystallized from a chloroform/ether/ethyl acetate mixture. The yield was 185 mg (0.37 mmoles).

M.p. 127°–129° C. $pK_a$=6.35 k'=0.6582 HR-MS-spectrum: m/e (relative intensity): 299 (21%), 267 (11%), 209 (20%), 208 (7%), 139 (49%), 96 (39%), 95 (100%). HPLC-MS (thermospray): m/e (relative intensity): 507 [M+1] (18%), 417 (6%), 337 (6%), 299 (66%), 267 (11%), 250 (11%), 209 (100%). NMR: δ 7.50 bs 2H, 6.73 bs 2H, 4.08 t 4H, 3.60 s 6H, 3.54 m 4H, 2.73 m 2H, 2.52 m 2H, 2.47 m 2H, 2.00 m 2H, 1.81 m 4H, 1.68 m 4H and 0.89 t 6H.

Example 8

O,O'-Dihydrogen (1,3-propylene) bispilocarpate (Formula I': Y=Y'=H; A=1,3-propylene)

The compound was prepared from the sodium salt of pilocarpine (1021 mg; 4.11 mmoles) and 1,3-dibromopropane (208 mg; 1.03 mmoles) with the method disclosed in Example 1. The bispilocarpate obtained was crystallized from an ethyl acetate/ether mixture. The yield was 330 mg (0.70 mmoles).

M.p. 71°–73° C. $pK_a$=6.40 k'=0.6139 HR-MS-spectrum: m/e (relative intensity): 303 (4%), 209 (46%), 208 (15%), 96 (27%), 95 (100%). HPLC-MS (thermospray): m/e (relative intensity): 493 [M+1] (25%), 417 (7%), 323 (9%), 285 (73%), 267 (9%), 250 (10%), 209 (100%). NMR: δ 7.50 bs 2H, 6.72 bs 2H, 4.19 t 4H, 3.60 s 6H, 3.54 m 4H, 2.72 m 2H, 2.53 m 2H, 2.49 m 2H, 1.99 m 2H, 2.08 qv 2H, 1.68 m 4H and 0.89 t 6H.

Example 9

O,O'-Diacetyl (1,4-xylylene) bispilocarpate (Formula I': Y=Y'=acetyl, A=1,4-xylylene; fumarate)

Into a mixture containing 679 mg (1.22 mmoles) of O,O'-dihydrogen (1,4-xylylene) bispilocarpate (see Example 1) and 2026 mg of potassium carbonate (14.66 mmoles) in toluene (150 ml), 767 mg (9.77 mmoles) of acetyl chloride were added dropwise during 30 to 40 hours. The mixture was stirred for 40 to 72 hours. To the reaction mixture a 2% sodium bicarbonate solution (150 ml) was added and the mixture was stirred at room temperature for 3 hours. The layers were separated and the toluene phase washed twice with water ($2 \times 150$ ml), was dried on calcium sulfate (30 min) and evaporated under reduced pressure, whereby O,O'-diacetyl (1,4-xylylene) bispilocarpate (free base) was obtained as an oil (780 mg, 1.22 mmoles). The oil was dissolved in toluene (20 ml) and a solution of fumaric acid (425 mg, 3.66 mmoles) in 2-propanol (10 ml) was added. The salt was precipitated with petroleum ether. The mixture was allowed to stand over night whereafter the O,O'-diacetyl (1,4-xylylene) bispilocarpate fumarate was isolated by filtering, whereby 750 mg (0.76 mmoles) of the fumarate salt were obtained.

$n_d^{20}=1.5230$ (free base) M.p. 58°–60° C. $pK_a=6.03$ k'=1.3987 HR-MS-spectrum: m/e (relative intensity): 638 (M+·) (5%), 565 (3%), 458 (22%), 443 (19%), 387 (24%), 208 (21%), 207 (45%), 96 (20%), 95 (100%). HR-MS=molecular weight=638.32739 (measured) 638.33156 (calculated) HPLC-MS (thermospray): m/e (relative intensity): 677 (35%), 661 (21%), 639 [M+1] (100%), 469 (13%), 431 (50%), 389 (37%), 209 (55%). NMR: δ 8.46 bs 2H, 7.41 s 4H, 7.19 bs 2H, 6.71 (fum.), 5.15 m 4H, 4.06 m 4H, 3.71 s 6H, 2.71 m 4H, 2.56 m 2H, 2.36 m 2H, 2.00 s 6H, 1.69 m 4H and 0.86 t 6H.

Example 10

O,O'-Dipropionyl (1,4-xylylene) bispilocarpate (Formula I': Y=Y'=propionyl; A=1,4-xylylene; fumarate)

The compound was prepared from O,O'-dihydrogen (1,4-xylylene) bispilocarpate (473 mg; 0.85 mmoles) (see Example 1) and propionyl chloride (631 mg; 6.82 mmoles) according to the method described in Example 9. The compound was crystallized from a 2-propanol/toluene/petroleum ether mixture. The yield was 730 mg (0.72 mmoles).

$n_d^{20}=1.5205$ (free base) M.p. 86°–89° C. $pK_a=5.80$ k'=2.3038 HR-MS-spectrum: m/e (relative intensity): 666 (M+·) (5%), 472 (53%), 457 (45%), 401 (58%), 209 (14%), 208 (13%), 207 (34%), 96 (43%), 95 (100%). HR-MS=molecular weight=666.35667 (measured) 666.36296 (calculated) HPLC-MS (thermospray): m/e (relative intensity): 705 (46%), 689 (22%), 667 [M+1] (100%), 459 (18%), 404 (11%), 351 (41%), 209 (80%). NMR: δ 8.39 bs 2H, 7.41 s 4H, 7.15 bs 2H, 6.72 (fum.), 5.15 m 4H, 4.07 m 4H, 3.69 s 6H, 2.71 m 4H, 2.55 m 2H, 2.36 m 2H, 2.30 q 4H, 1.69 m 4H, 1.08 t 6H, 0.86 t 6H.

Example 11

O,O'-Dibutyryl 1,4-xylylene) bispilocarpate (Formula I': Y=Y'=butyryl; A=1,4-xylylene; fumarate)

The compound was prepared from O,O'-dihydrogen (1,4-xylylene) bispilocarpate (431 mg; 0.78 mmoles) (see Example 1) and butyryl chloride (663 mg; 6.22 mmoles) according to the method described in Example 9. The compound was crystallized from a 2-propanol/toluene/petroleum ether mixture. The yield was 800 mg (0.77 mmoles).

$n_d^{20}=1.5070$ (free base) M.p.=90°–92° C. $pK_a=6.00$ k'=4.0127 HR-MS-spectrum: m/e (relative intensity): 694 (M+·) (3%), 486 (26%), 471 (14%), 415 (17%), 209 (15%), 208 (20%), 207 (37%), 96 (26%), 95 (100%). HR-MS=molecular weight=694.39378 (measured) 694.39415 (calculated) HPLC-MS (thermospray): m/e (relative intensity): 732 (77%), 717 (36%), 695 [M+1] (100%), 525 (9%), 487 (13%), 455 (7%), 417 (14%), 297 (7%), 209 (28%). NMR: δ 8.51 bs 2H, 7.41 s 4H, 7.21 bs 2H, 6.71 (fum.), 5.15 m 4H, 4.07 m 4H, 3.72 s 6H, 2.72 m 4H, 2.55 m 2H, 2.36 m 2H, 2.27 t 4H, 1.69 m 4H, 1.59 m 4H, 0.91 t 6H and 0.86 t 6H.

Example 12

O,O'-Divaleryl (1,4-xylylene) bispilocarpate (Formula I': Y=Y'=valeryl; A=1,4-xylylene; fumarate)

The compound was prepared from O,O'-dihydrogen (1,4-xylylene) bispilocarpate (395 mg; 0.71 mmoles) (see Example 1) and valeryl chloride (685 mg; 5.68 mmoles) according to the method described in Example 9. The compound was recrystallized from a 2-propanol/toluene/petroleum ether mixture. The yield was 567 mg (0.53 mmoles).

$n_d^{20}=1.5080$ (free base) M.p. =84°–86° C. $pK_a=6.00$ k'=7.3861 HR-MS-spectrum: m/e (relative intensity): 722 (M+·) (9%), 500 (60%), 485 (31%), 429 (41%), 209 (14%), 208 (17%), 207 (34%), 96 (46%), 95 (100%). HR-MS=molecular weight=722.42308 (measured) 722.42546 (calculated) HPLC-MS (thermospray): m/e (relative intensity): 761 (86%), 745 (33%), 723 [M+1] (100%), 431 (16%), 362 (9%), 209 (35%). NMR: δ 8.35 bs 2H, 7.41 s 4H, 7.13 bs 2H, 6.72 (fum.), 5.15 m 4H, 4.07 m 4H, 3.69 s 6H, 2.70 m 4H, 2.55 m 2H, 2.36 m 2H, 2.29 t 4H, 1.69 m 4H, 1.55 m 4H, 1.33 m 4H, 0.91 t 6H and 0.86 t 6H.

Example 13

O,O'-Dicyclopropylcarbonyl (1,4-xylylene) bispilocarpate (Formula I': y=y,=cyclopropylcarbonyl, A=1,4-xylylene; fumarate)

The compound was prepared from O,O'-dihydrogen (1,4-xylylene) bispilocarpate (547 mg; 0.99 mmoles) (see Example 1) and cyclopropylcarbonyl chloride (788 mg; 7.92 mmoles) according to the method described in Example 9. The compound was crystallized from a 2-propanol/toluene/petroleum ether mixture. The yield was 843 mg (0.81 mmoles).

$n_d^{20}=1.5290$ (free base) M.p.=73°–75° C. $pK_a=6.00$ k'=2.4684 HR-MS-spectrum: m/e (relative intensity): 690 (M+·) (5%), 484 (36%), 469 (19%), 413 (30%), 209 (7%), 208 (16%), 207 (46%), 96 (30%), 95 (100%).

HR-MS=molecular weight=690.36014 (measured) 690.36286 (calculated) HPLC-MS (thermospray): m/e (relative intensity): 728 (89%), 713 (42%), 691 [M+1] (100%), 623 (12%), 521 (23%), 480 (30%), 453 (32%), 415 (46%), 209 (73%). NMR: δ 8.55 bs 2H, 7.41 s 4H, 7.24 bs 2H, 6.71 (fum.), 5.16 m 4H, 4.08 m 4H, 3.73 s 6H, 2.74 m 4H, 2.57 m 2H, 2.38 m 2H, 1.70 m 4H, 1.69 m 2H, 0.87 t 6H and 0.86 m 8H.

Example 14

O,O'-Dibenzoyl (1,4-xylylene) bispilocarpate (Formula I': Y=Y'=benzoyl, A=1,4-xylylene; fumarate)

The compound was prepared from O,O'-dihydrogen (1,4-xylylene) bispilocarpate (486 mg; 0.88 mmoles) (see Example 1) and benzoyl chloride (990 mg; 7.04 mmoles) according to the method described in Example 9. The compound was crystallized from a 2-propanol/toluene/petroleum ether mixture. The yield was 464 mg (0.42 mmoles).

$n_d^{20}$=1.5605 (free base) M.p.=72°–75° C. $pK_a$=5.80 k'=5.9304 HR-MS-spectrum: m/e (relative intensity): 762 (M+·) (1%), 243 (10%), 208 (15%), 207 (38%), 96 (26%), 95 (100%). HR-MS=molecular weight=762.36774 (measured) 762.36286 (calculated) HPLC-MS (thermospray): m/e (relative intensity): 785 (28%), 763 [M+1](100%), 593 (16%), 555 (21%), 489 (7%), 451 (8%), 209 (42%). NMR: δ 8.41 bs 2H, 7.93 m 4H, 7.60 m 2H, 7.46 m 4H, 7.32 s 4H, 7.20 bs 2H, 6.71 (fum.), 5.07 m 4H, 4,32 m 4H, 3.71 s 6H, 2.82 m 4H, 2.65 m 2H, 2.53 m 2H, 1.75 m 4H and 0.89 t 6H.

Example 15

O,O'-Adipoyl (dibenzyl) bispilocarpate (Formula I'': R=R'=benzyl, B=1,4-butylene; fumarate)

Into a solution containing 7.78 mmoles (1932 mg) of pilocarpic acid sodium salt, the preparation of which is disclosed in the Example 1, in 60 ml of dimethyl sulfoxide, 7.78 mmoles of benzyl chloride (985 mg) were added within about one hour. The solution was stirred at room temperature for 48 to 72 hours, and poured into 100 ml of distilled water. The mixture was extracted with two portions of 100 ml ethyl acetate. The combined ethyl acetate extracts were washed with 150 ml of distilled water, 150 ml of a 2% sodium bicarbonate solution and 150 ml of distilled water. The ethyl acetate extracts were dried with calcium sulfate and the ethyl acetate was evaporated under reduced pressure to produce pilocarpic acid benzyl ester. The ester was crystallized from a chloroform/petroleum ether mixture, whereby 1125 mg (5.56 mmoles) of the ester were obtained.

M.p.=101°–104° C. $pK_a$=6.50 k'=0.7658 HR-MS-spectrum: m/e (relative intensity): 208 (15%), 96 (45%), 95 (100%). HR-MS=molecular weight=no M+-peak HPLC-MS (thermospray):m/e (relative intensity): 317 [M+1] (51%), 209 (100%) NMR: δ 7.47 bs 1H, 7.33 m 5H, 6.69 bs 1H, 5.10 s 2H, 3.52 m 2H, 3.47 s 3H, 2.70 m 1H, 2.52 m 1H, 2.45 m 1H, 1.98 m 1H, 1.70 m 2H and 0.86 t 3H.

Into a mixture containing 406 mg (1.28 mmoles) of pilocarpic acid benzyl ester and 553 mg (3.00 mmoles) of potassium carbonate in toluene (40 ml) adipoyl chloride (108 mg; 0.59 mmoles) was added dropwise within about 24 hours. The solution was stirred at room temperature about for 48 hours. To the reaction mixture a 2% sodium bicarbonate solution (40 ml) was added and the mixture was stirred at room temperature for 3 hours. The layers were separated and the toluene phase was washed twice with distilled water (2×50 ml), dried on calcium sulfate (30 min) and evaporated under reduced pressure, whereby O,O'-adipoyl (dibenzyl) bispilocarpate (free base) was obtained as an oil (324 mg; 0.44 mmoles). The oil was dissolved in toluene (15 ml) and a solution of fumaric acid (153 mg; 1.32 mmoles) in 2-propanol (5 ml) was added. The salt was precipitated with petroleum ether. The mixture was allowed to stand over night whereby O,O'-adipoyl (dibenzyl) bispilocarpate fumarate (327 mg; 0.30 mmoles) was obtained.

$n_d^{20}$=1.5340 (free base) M.p.=98°–100° C. $pK_a$=6.00 k'=4.4810 HR-MS-spectrum: m/e (relative intensity): 742 (M+·) (5%), 741 (8%), 629 (39%), 625 (52%), 536 (75%), 535 (100%), 459 (69), 445 (43%), 357 (33%), 299 (45%), 209 (55%), 207 (64%), 95 (69%), 91 (56%). HR-MS=molecular weight=742.390380 (measured) 742.394150 (calculated) HPLC-MS (thermospray): m/e (relative intensity): 780 (75%), 765 (28%), 743 [M+1] (100%), 480 (8%), 445 (10%), 317 (23%), 209 (26%). NMR: δ 8.36 bs 2H, 7.35 m 10H, 7.14 bs 2H, 6.72 (fum.), 5.14 m 4H, 4.07 m 4H, 3.65 s 6H, 2.68 m 4H, 2.54 m 2H, 2.34 m 2H, 2.30 t 4H, 1.69 m 4H, 1.59 t 4H and 0.87 t 6H.

Example 16

O,O'-Glutaryl (dibenzyl) bispilocarpate (Formula I'': R=R'=benzyl, B=1,3-propylene; fumarate)

The compound was prepared from pilocarpic acid benzyl ester (633 mg; 2.00 mmoles) and glutaryl chloride (135 mg; 0.80 mmoles) according to the method described in Example 15. The compound was crystallized from a 2-propanol/toluene/petroleum ether mixture. The yield was 477 mg (0.44 mmoles).

$n_d^{20}$=1.5330 (free base) M.p.=55°–58° C. $pK_a$=6.00 k'=3.7658 HR-MS-spectrum: m/e (relative intensity): 728 (M+·) (0,15%), 419 (8%), 343 (16%), 209 (12%), 208 (14%), 207 (45%), 96 (31%), 95 (76%), 91 (100%) HR-MS=molecular weight=728.3734740 (measured) 728.3785152 (calculated) HPLC-MS (thermospray): m/e (relative intensity): 729 [M+1] (36%), 431 (45%), 317 (35%), 209 (100%). NMR: δ 8.47 bs 2H, 7.35 m 10H, 7.20 bs 2H, 6.71 (fum.), 5.14 m 4H, 4.07 m 4H, 3.67 s 6H, 2.68 m 4H, 2.54 m 2H, 2.34 t 4H, 2.32 m 2H, 1.84 m 2H, 1.69 m 4H and 0.87 t 6H.

Example 17

O,O'-Succinyl (dibenzyl) bispilocarpate (Formula I'': R=R'=benzyl, B=ethylene; fumarate)

The compound was prepared from pilocarpic acid benzyl ester (633 mg; 2.00 mmoles) and succinyl chloride (124 mg; 0.80 mmoles) according to the method described in the Example 15. The compound was crystallized from a 2-propanol/toluene/petroleum ether mixture. The yield was 402 mg (0.38 mmoles).

$n_d^{20}$=1.5360 (free base) M.p.=65°–67° C. $pK_a$=6.00 k'=3.4557 HR-MS-spectrum: m/e (relative intensity): 714 (M+·) (1%), 537 (10%), 415 (9%), 329 (11%), 208 (10%), 207 (31%), 96 (23%), 95 (94%), 91 (100%) HR-MS=molecular weight=714.3668980 (measured) 714.3628652 (calculated) HPLC-MS (thermospray): m/e (relative intensity): 751 (10%), 715 [M+1] (47%), 417 (32%), 317 (57%), 209 (100%). NMR: δ 8.44 bs 2H, 7.35 m 10H, 7.17 bs 2H, 6.71 (fum.), 5.14 m 4h, 4.09 m 4H, 3.65 s 6H, 2.68 m 4H, 2.58 s 4H, 2.53 m 2H, 2.32 m 2H, 1.69 m 4H and 0.86 t 6H.

Example 18

O,O'-Fumaroyl (dibenzyl) bispilocarpate (Formula I'': R=R'=benzyl, B=ethenylene; fumarate)

The compound was prepared from pilocarpic acid benzyl ester (633 mg; 2.00 mmoles) and fumaroyl chloride (122 mg; 0.80 mmoles) according to the method described in Example 15. The compound was crystallized from a 2-propanol/toluene/petroleum ether mixture. The yield was 112 mg (0.11 mmoles).

$n_d^{20}$=1.5415 (free base) M.p.=64°-66° C. $pK_a$=6.05 k'=4.2785 HR-MS-spectrum: m/e (relative intensity): 712 (M+·) (0,4%), 411 (41%), 407 (34%), 318 (56%), 317 (96%), 299 (39%), 209 (67%), 207 (40%), 96 (47%), 95 (100%), 91 (62%). HR-MS=molecular weight=712.3462220 (measured), 20 eV 712.3472151 (calculated) HPLC-MS (thermospray): m/e (relative intensity): 750 (40%), 733 (20%), 713 [M+1] (100%), 450 (15%), 413 (32%), 317 (96%), 209 (42%).

Example 19

O,O'-Terephthaloyl (dibenzyl) bispilocarpate (Formula I'': R=R'=benzyl, B=p-phenylene; fumarate)

The compound was prepared from pilocarpic acid benzyl ester (633 mg; 2.00 mmoles) and terephthaloyl chloride (162 mg; 0.80 mmoles) according to the method described in Example 15. The compound was crystallized from a 2-propanol/toluene/petroleum ether mixture. The yield was 370 mg (0.33 mmoles).

$n_d^{20}$=1.5510 (free base) M.p.=130°-133° C. $pK_a$=6.00 k'=7.3354 HR-MS-spectrum: m/e (relative intensity): 762 (M+·) (1%), 208 (13%), 207 (46%), 96 (36%), 95 (100%), 91 (70%). HR-MS=molecular weight=762.3563840 (measured) 762.3628652 (calculated) HPLC-MS (thermospray): m/e (relative intensity): 763 [M+1] (82%), 465 (52%), 317 (97%), 267 (23%), 209 (100%). NMR: δ 8.46 bs 2H, 8.05 s 4H, 7.32 m 10H, 7.24 bs 2H, 6.72 (fum.), 5.10 m 4H, 4.37 m 4H, 3.70 s 6H, 2.83 m 4H, 2.66 m 2H, 2.54 m 2H, 1.75 m 4H and 0.91 t 6H.

Example 20

O,O'-Dicyclopropylcarbonyl (1,6-hexylene) bispilocarpate (Formula I': Y=Y'=cyclopropylcarbonyl, A=1,6-hexylene; fumarate)

The compound was prepared from O,O'-dihydrogen (1,6-hexylene) bispilocarpate (600 mg; 1.12 mmoles) (see Example 5) and cyclopropylcarbonyl chloride (766 mg; 7.33 mmoles) according to the method described in Example 9. The compound was crystallized from a 2-propanol/toluene/petroleum ether mixture. The yield was 620 mg (0.61 mmoles).

$n_d^{20}$=1.5020 (free base) M.p.=60°-63° C. (fumarate salt) $pK_a$=6.00 (free base) HR-MS-spectrum: m/e (relative intensity): 670 (M+·) (2%), 464 (13%), 449 (10%), 337 (10%), 209 (10%), 207 (21%), 96 (53%), 95 (100%). HR-MS=molecular weight=HPLC-MS (thermospray): m/e (relative intensity): 671 [M+1] (100%), NMR: δ 8.53 bs 2H, 7.24 bs 2H, 6.72 (fum.), 4.12 bm 8H, 3.81 s 6H, 2.77 m 4H, 2.52 m 2H, 2.38 m 2H, 1.70 m 8H, 1.61 m 2H, 1.45 m 4H, 0.91 m 6H, 0.90 m 8H.

Example 21

O,O'-Dicyclopropylcarbonyl (1,5-pentylene) bispilocarpate (Formula I': Y=Y'-cyclopropylcarbonyl, A=1,5-pentylene; fumarate)

The compound was prepared from O,O'-dihydrogen (1,5-pentylene) bispilocarpate (424 mg; 0.82 mmoles) (see Example 6) and cyclopropylcarbonyl chloride (682 mg; 6.52 mmoles) according to the method described in Example 9. The compound was crystallized from a 2-propanol/toluene/petroleum ether mixture. The yield was 230 mg (0.23 mmoles).

$n_d^{20}$=M.p.=56°-59° C. $pK_a$=HR-MS-spectrum: m/e (relative intensity): 656 (M+·) (3%), 450 (39%), 435 (23%), 379 (13%), 363 (13%), 209 (15%), 207 (29%), 96 (50%), 95 (100%). HPLC-MS (Thermospray): m/e (relative intensity): 657 [M+1] (92%), NMR: δ 8.34 bs 2H, 7.15 bs 2H, 6.71 (fum.), 4.12 bm 8H, 3.77 s 6H, 2.77 m 4H, 2.51 m 2H, 2.38 m 2H, 1.71 m 8H, 1.61 m 2H, 1.48 m 4H, 0.91 m 6H, 0.88 m 8H.

Example 22

O,O'-Dihydrogen (1,2-ethylene) bispilocarpate (Formula I'Y=hydrogen, A=1,2-ethylene)

The monoester was prepared by adding 247 mg (1.31 mmoles) of 1,2-dibromoethane dropwise to a solution containing 1302 mg (5.25 mmoles) pilocarpic acid sodium salt in 60 ml of dimethyl sulfoxide. The solution was mixed at room temperature for 72 hours and poured into 100 ml of distilled water. The mixture was extracted with two portions of each 100 ml of chloroform. The combined chloroform extracts were washed with 100 ml of distilled water, with 100 ml of 2% sodium bicarbonate solution and with 100 ml of distilled water. The chloroform extracts were dried on calcium sulfate (30 min) and the chloroform evaporated under reduced pressure, and the bispilocarpate obtained was crystallized from a ethyl acetate/ether mixture, whereby 332 mg (0.69 mmoles) of the title compound were obtained.

M.p.=111°-115° C $pK_a$=6.30 HR-MS-spectrum: m/e (relative intensity): 209 (8%), 208 (19%), 96 (30%), 95 (100%). NMR: δ 7.49 2H bs, 6.74 2H bs, 4.30 4H m, 3.60 6H s, 3.54 4H m, 2.73 2H m, 2.56 2H m, 2.51 2H m, 2.02 2H m, 1.68 4H m, 0.89 6H t.

Correspondingly, O,O'-dihydrogen (2-hydroxy-1,3-propylene) bispilocarpate may be prepared from the sodium salt of pilocarpic acid (1674 mg; 6.75 mmoles) and 1,3-dibromo-2-hydroxypropane (341 mg; 1.69 mmoles).

O,O'-dihydrogen (2-hydroxy-1,3-propylene) bispilocarpate can also be prepared from the sodium salt of pilocarpic acid and epichlorohydrine (2:1).

Example 23

O,O'-Dicyclopropyl carbonyl (1,2-ethylene) bispilocarpate (Formula I'Y=cyclopropylcarbonyl; A=1,2-ethylene)

The compound was prepared by adding 945 mg (9.64 mmoles) of cyclopropylcarbonyl chloride dropwise during ca. 24 hours to a mixture containing O,O'-dihydrogen (1,2-ethylene) bispilocarpate (540 mg; 1.13 mmoles) (see Example 22) and 1866 mg potassium carbonate (13.5 mmoles) in toluene (150 ml). The mixture was stirred for 24–72 hours. To the reaction mixture a 2% sodium bicarbonate solution (150 ml) was added and the mixture was stirred at room temperature for 3 hours. The layers were separated and the toluene phase washed twice with water (2×150 ml), was dried on calcium sulfate (30 min) and evaporated under reduced pressure, whereby O,O'-dicyclopropylcarbonyl (1,2-ethylene) bispilocarpate was obtained. The yield was 304 mg (0.49 mmoles).

$pK_a$=5.70 HR-MS-spectrum: m/e (relative intensity): 614 [M+·] (1%), 408 (11%), 393 (10%), 321 (7%), 320 (29%), 307 (9%), 291 (16%), 209 (18%), 208 (11%), 207 (78%), 163 (29%), 162 (14%), 121 (47%), 113 (52%), 96 (38%), 95 (100%). HR-MS: molecular weight=614.3299260 (measured) 614.3315650 (calculated). NMR: δ 7.56 2H bs, 6.78 2H bs, 4.35 4H m, 4.08 4H m, 3.63 6H s, 2.69 4H m, 2.50 2H m, 2.33 2H m, 1.69 4H m, 1.61 2H m, 1.10 6H t, 0,92 6H t, 0.90 8H m.

Example 24

O,O'-Dipropionyl (1,2-ethylene) bispilocarpate (Formula I', Y=propionyl, A=1,2-ethylene)

The compound was prepared from O,O'-dihydrogen (1,2-ethylene) bispilocarpate (300 mg; 0.63 mmoles) (see Example 22) and propionyl chloride (464 mg; 5.02 mmoles) according to the method described in Example 23. The yield was 243 mg (0.41 mmoles).

$pK_a$=6.00 HR-MS-spectrum: m/e (relative intensity): 591 (5%), 590 [M+·](5%), 503 (7%), 397 (19%), 396 (85%), 395 (8%), 382 (20%), 381 (95%), 309 (11%), 209 (18%), 195 (45%), 121 (18%), 96 (78%), 95 (100%). HR-MS: molecular weight=590.3363040 (measured) 590.3315650 (calculated). NMR: δ 7.61 2H bs, 6.78 2H bs, 4.33 4H m, 4.08 4H m, 3.62 6H s, 2.68 4H m, 2.49 2H m, 2.32 2H q, 1.68 4H m, 1.10 6H t, 0.90 6H t.

Example 25

O,O'-Dicyclobutylcarbonyl (1,2-ethylene) bispilocarpate (Formula I', Y=cyclobutylcarbonyl, A 1,2-ethylene; fumarate)

The compound was prepared from O,O'-dihydrogen (1,2-ethylene) bispilocarpate (470 mg; 0.98 mmoles) (see Example 22) and cyclobutylcarbonyl chloride (931 mg; 7.86 mmoles) according to the method described in Example 23. The fumarate salt was crystallized according to Example 9 from a 2-propanol/toluene/petroleum ether mixture. The yield was 810 mg (0.82 mmoles).

M.p.=49°–51° C. (fum.) HR-MS-spectrum: m/e (relative intensity): 642 [M+·](4%), 529 (6%), 436 (10%), 423 (22%), 422 (100%), 421 (13%), 408 (18%), 407 (85%), 335 (10%), 221 (52%), 209 (12%), 121 (13%), 96 ( 86%), 95 ( 50%) . HR-MS: molecular weight=642.3648680 (measured) 642.3628651 (calculated) NMR: δ 8.50 2H bs, 7.23 2H bs, 6.73 s (fum.), 4.36 4H m, 4.11 4H m, 3.79 6H s, 3.16 2H m, 2.77 4H m, 2.54 2H m, 2.40 2H m, 2.22 4H m, 2.01 4H m, 1.89 4H m, 1.71 4H m, 0.93 6H t.

Example 26

O,O'-Dipropionyl (1,3-propylene) bispilocarpate (Formula I'Y=propionyl, A=1,3-propylene)

The compound was prepared from O,O'-dihydrogen (1,3-propylene) bispilocarpate (500 mg; 1.02 mmoles) (see Example 22) and propionyl chloride (751 mg; 8.12 mmoles) according to the method described in Example 23. The yield was 467 mg (0.77 mmoles).

$pK_a$=5.95 HR-MS-spectrum: m/e (relative intensity): 604 [M+·](6%), 517 (7%), 411 (13%), 410 (57%), 396 (16%), 395 (71%), 339 (36%), 209 (15%), 208 (6%), 195 (48%), 121 (20%), 96 (56%), 95 (100%). HR-MS: molecular weight=604.3491210 (measured) 604.3472151 (calculated). NMR: δ 7.56 2H bs, 6.76 2H bs, 4.18 4H m, 4.08 4H m, 3.62 6H s, 2.69 4H m, 2.49 2H m, 2.33 2H m, 2.31 4H q, 2.01 4H qv, 1.68 4H m, 1.10 6H t, 0.91 6H t.

Example 27

O,O'-Dicyclopropylcarbonyl (1,3-propylene) bispilocarpate (Formula I', Y=cyclopropylcarbonyl, A=1,3-propylene)

The compound was prepared from O,O'-dihydrogen (1,3-propylene) bispilocarpate (422 mg; 0.86 mmoles) (see Example 1) and cyclopropylcarbonyl chloride (719 mg; 6.88 mmoles) according to the method described in Example 2. The yield was 297 mg (0.47 mmoles).

$pK_a$=6.05 HR-MS-spectrum: m/e (relative intensity): 629 (4%), 628 [M+·] (7%), 423 (19%), 422 (76%), 408 (16%), 407 (73%), 352 (10%), 351 (40%), 335 (9%), 334 (9%), 209 (19%), 208 (11%), 207 (73%), 121 (32%), 96 (55%), 95 (100%). HR-MS: molecular weight=628.3428340 (measured) 628.3472151 (calculated). NMR: δ 7.51 2H bs, 6.73 2H bs, 4.19 4H m, 4.07 4H m, 3.61 6H s, 2.68 4H m, 2.49 2H m, 2.33 2H m, 2.02 2H qv, 1.68 4H m, 0.91 6H t, 0.90 8H m.

Example 28

O,O'-Dicyclobutylcarbonyl (1,3-propylene) bispilocarpate (Formula I'Y=cyclobutylcarbonyl, A=1,3-propylene, fumarate)

The compound was prepared from O,O'-dihydrogen (1,3-propylene) bispilocarpate (705 mg; 1.43 mmoles) (see Example 22) and cyclobutylcarbonyl chloride (1357 mg; 11.45 mmoles) according to the method described in the Example 23. The fumarate salt was crystallized according to Example 9. The yield was 960 mg (0.96 mmoles).

M.p.=33°–35° C (fum.) HR-MS-spectrum: m/e (relative intensity): 657 (4%), 656 [M+·] (6%), 543 (9%), 437 (23%), 436 (100%), 422 (22%), 421 (86%), 366 (10%), 365 (46%), 222 (9%), 221 (58%), 209 (14%), 121 (15%), 96 (68%), 95 (78%). HR-MS: molecular weight=656.3743290 (measured) 656.3785152 (calculated). NMR: δ 8.50 2H bs, 7.23 2H bs, 6.73 s (fum.), 4.21 4H m, 3.80 6H s, 3.16 2H m, 2.78 4H m, 2.53 2H m, 2.40 2H m, 2.22 4H m, 2.03 2H qv, 2.01 4H m, 1.89 4H m, 1.71 4H m, 0.92 6H t.

Correspondingly, O,O'-dipropionyl (2-hydroxy-1,3-propylene) bispilocarpate may be prepared according to Example 23 from O,O'-dihydrogen (2-hydroxy-1,3-propylene) bispilocarpate (544 mg; 1.07 mmoles) (see Example 22) and propionyl chloride (785 mg; 8.49 mmoles).

Example 29

O,O'-Dipivalyl (1,2-ethylene) bispilocarpate (Formula I'Y=pivalyl, A=1,2-ethylene, fumarate)

The compound was prepared from O,O'-dihydrogen (1,2-ethylene) bispilocarpate (384 mg; 0.80 mmoles; see Example 22) and pivalyl chloride (772 mg; 6.41 mmoles) according to the method disclosed in Example 23. The fumarate salt was crystallized according to Example 9 from 2-propanol/toluene/petroleum ether. Yield 293 mg (0.29 mmoles).

M.P.=61°-65° C. (fum.) HR-MS-spectrum: m/e (relative intensity): 647 (5%), 646 [M+·] (7%), 645 (3%), 631 (6%), 531 (6%), 425 (24%), 424 (91%), 410 (17%), 409 (67%), 337 (9%), 293 (7%), 223 (34%), 209 (9%), 163 (9%), 123 (10%), 122 (5%), 121 (29%), 96 (84%), 95 (100%). HR-MS: molecular weight=646. 39318800 (measured) 646.39416531 (calculated). NMR: δ 8.51 2H bs, 7.23 2H bs, 6.73 s (fum.), 4.37 4H m, 4.10 4H m, 3.80 6H s, 2.78 4H m, 2.55 2H m, 2.39 2H m, 1.71 4H m, 1.20 18H s, 0.93 6H t.

Example 30

O,O'-Dicyclopentylcarbonyl (1,3-propylene) bispilocarpate (Formula I'Y=cyclopentylcarbonyl, A=1,3-propylene, fumarate)

The compound was prepared from O,O'-dihydrogen (1,3-propylene) bispilocarpate (401 mg; 0.81 mmoles; see Example 22) and cyclopentylcarbonyl chloride (859 mg; 6.48 mmoles) according to the method disclosed in Example 23. The compound was crystallized from a 2-propanol/toluene/petroleum ether mixture. Yield 501 mg (0.48 mmoles).

M.P.=The compound is hygroscopic HR-MS-spectrum: m/e (relative intensity): 685 (4%), 684 [M+·] (6%), 683 (2%), 451 (11%), 450 (48%), 436 (7%), 435 (25%), 379 (15%), 235 (29%), 209 (12%), 163 (12%), 121 (31%), 96 (47%), 95 (100%). HR-MS: molecular weight=684.4060820 (measured) 684.4098154 (calculated). NMR: δ 8.57 2H bs, 7.27 2H bs, 6.72 s (fum.), 4.21 4H t, 4.10 4H d, 3.81 6H s, 2.80 4H m, 2.75 2H m, 2.54 2H m, 2.40 2H m, 2.03 2H qv, 1.88 4H m, 1.74 4H m, 1.71 4H m, 1.62 8H m, 0.92 6H t.

Example 31

O,O'-Dicyclohexylcarbonyl (1,3-propylene) bispilocarpate (Formula I', Y=cyclohexylcarbonyl, A=1,2-ethylene, fumarate)

The compound was prepared from O,O'-dihydrogen (1,3-propylene) bispilocarpate (424 mg; 0.86 mmoles; see Example 22) and cyclohexylcarbonyl chloride (1009 mg; 6.88 mmoles) according to the method disclosed in Example 23. The compound was crystallized from a 2-propanol /toluene/petroleum ether mixture. Yield 722 mg (0.68 mmoles).

M.P.=50°-53° C. HR-MS-spectrum: m/e (relative intensity): 713 (2%), 712 [M+·] (6%), 711 (3%), 465 (16%), 464 (54%), 450 (9%), 449 (31%), 394 (5%), 393 (18%), 250 (6%), 249 (33%), 209 (12%), 163 (12%), 121 (32%), 96 (56%), 95 (100%). HR-MS: molecular weight=712.4428410 (measured) 712.4411156 (calculated). NMR: δ 8.55 2H bs, 7.26 2H bs, 6.71 s (fum.), 4.20 4H t, 4.09 4H d, 3.81 6H s, 2.79 4H m, 2.54 2H m, 2.39 2H m, 2.32 2H m, 2.03 2H qv, 1.87 4H m, 1.74 4H m, 1.72 4H m, 1.70 4H m, 1.38 8H m, 0.92 6H t.

Example 32

O,O'-Succinyl (diethyl) bispilocarpate (Formula I'',R=R'=ethyl, B=1,2-ethylene)

9.80 mmoles of ethylbromide (1068 mg) were added dropwise within about an hour to a solution containing 9.80 mmoles (2432 mg) of pilocarpic acid sodium salt in 60 ml of dimethyl sulfoxide. The solution was stirred at room temperature for 48-72 hours and poured into 100 ml of distilled water. The mixture was extracted with two portions of each 150 ml of ethyl acetate. The combined ethyl acetate extracts were washed with 150 ml of distilled water, with 150 ml of 2% sodium bicarbonate solution and with 150 ml of distilled water. The ethyl acetate extracts were dried on calcium sulfate (30 min) and the ethyl acetate evaporated under reduced pressure, and the pilocarpic acid ethyl ester obtained was crystallized from a chloroform/ petroleum ether-mixture, whereby 448 mg (1.76 mmoles) of the ester were obtained.

M.p.=104°-107° C. pK$_a$=6.60 HR-MS-spectrum: m/e (relative intensity): 254 [M+] (17%), 236 (18%), 223 (11%), 209 (24%), 207 (11%), 163 (14%), 139 (46%), 121 (31%), 96 (53%), 95 (100%). HR-MS: molecular weight=254.1620180 (measured) 254.1630428 (calculated) NMR: δ 7.49 1H bs, 6.74 1H bs, 4.13 2H m, 3.61 3H s, 3.55 2H m, 2.73 1H m, 2.53 1H m, 2.50 1H m, 2.03 2H m, 1.68 2H m, 1.27 3H t, 0.90 3H t.

Succinyl chloride (98 mg; 0.63 mmoles) was added dropwise within about 24 hours to a mixture containing 401 mg of pilocarpic acid ethyl ester and 873 mg (6.32 mmoles) calcium carbonate in toluene (50 ml). The solution was stirred at room temperature for ca. 48 hours. To the reaction mixture 2% sodium bicarbonate solution (50 ml) was added and the mixture was stirred at room temperature for 3 hours. The layers were separated and the toluene phase washed twice with distilled water (2 x 100), was dried on calcium sulfate (30 min) and evaporated under reduced pressure, whereby O,O'-succinyl (diethyl) bispilocarpate (192 mg; 0.32 mmoles) was obtained. HR-MS-spectrum: m/e (relative intensity): 590 [M+] (9%), 545 (12%), 476 (24%), 475 (90%), 424 (13%), 409 (7%), 237 (9%), 223 (12%), 209 (7%), 163 (9%), 121 (100%), 96 (39%), 95 (82%). HR-MS: molecular weight=590.3260650 (measured) 590.3315650 (calculated) NMR: δ 7.50 2H bs, 6.75 2H bs, 4.16 4H m, 4.12 4H m, 3.61 6H s, 2.68 4H m, 2.62 4H m, 2.46 2H m, 2.29 2H m, 1.67 4H m, 1.28 6H t, 0.91 6H t The starting material, the sodium salt of pilocarpic acid, may be prepared according to Example 1.

Example 33

O,O'-Glutaryl (diethyl) bispilocarpate (Formula I''R=R'=ethyl, B=1,3-propylene)

The compound was prepared from the ethyl ester of pilocarpine (589 mg; 2.32 mmoles) and glutaryl chloride (157 mg; 0.93 mmoles) according to Example 32. Yield 152 mg (0.25 mmoles).

HR-MS-spectrum: m/e (relative intensity): 604 [M+] (7%), 559 (11%), 490 (21%), 489 (75%), 237 (9%), 223 (6%), 209 (8%), 163 (10%), 123 (6%), 122 (10%), 121 (100%), 96 (26%), 95 (61%). HR-MS: molecular weight=604.3478240 (measured) 604.3472151 (calculated) NMR: δ 7.53 2H bs, 6.74 2H bs, 4.13 4H m, 4.08 4H m, 3.61 6H s, 2.67 4H m, 2.45 2H m, 2.39 4H m, 2.30 2H m, 1.89 2H m, 1.67 4H m, 1.26 6H t, 0.90 6H t

Example 34

O,O'-Adipoyl (diethyl) bispilocarpate (Formula I'',R=R'=ethyl, B=1,4-butylene)

The compound was prepared from the ethyl ester of pilocarpine (609 mg; 2.40 mmoles) and adipoyl chloride (176 mg; 0.96 mmoles) according to Example 32. Yield 259 mg (0.42 mmoles).

HR-MS-spectrum: m/e (relative intensity): 618 [M+] (10%), 573 (9%), 504 (20%), 503 (67%), 489 (10%), 368 (10%), 365 (17%), 295 (9%), 249 (29%), 237 (11%), 236 (24%), 223 (15%), 209 (18%), 207 (20%), 163 (21%), 123 (9%), 122 (12%), 121 (100%), 96 (51%). HR-MS: molecular weight=618.3625030 (measured) 618.3628652 (calculated) NMR: δ 7.53 2H bs, 6.73 2H bs, 4.13 4H m, 4.08 4H m, 3.61 6H s, 2.67 4H m, 2.47 2H m, 2.34 4H m, 2.30 2H m, 1.68 4H m, 1.63 4H m, 1.26 6H t, 0.90 6H t

Example 35

O,O'-Dipivaloyl (1,4-Xylylene) bispilocarpate (Formula I': Y=Y'=pivaloyl; A=1,4-xylylene; fumarate)

The compound was prepared from O,O'-dihydrogen (1,4-xylylene) bispilocarpate (155 mg; 0.28 mmoles) (see Example 1) and pivaloyl chloride (270 mg; 2,24 mmoles) according to the method described in the Example 9. The compound was crystallized from a 2-propanol/toluene/petroleum ether mixture. The yield was 120 mg (0.11 mmoles).

M.p. 75°-77° C. HR-MS-spectrum: m/e (relative intensity): 722 (M+·)(32%), 707 (13%), 621 (18%), 500 (16%), 429 (11%), 223 (21%), 208 (23%), 207 (62%), 96 (33%), 95 (100%). HR-MS=molecular weight=722.4262540 (measured) 722.4254655 (calculated) NMR: δ 8.30 bs 2H, 7.41 s 4H, 7.10 bs 2H, 6.73 s (fum.), 5.15 m 4H, 3.68 s 6H, 2.70 m 4H, 2.56 m 2H, 2.35 m 2H, 1.69 m 4H, 1.18 s 18H, 0.87 t 6H.

We claim:

1. Bispilocarpic acid ester derivative of the formula (I) wherein

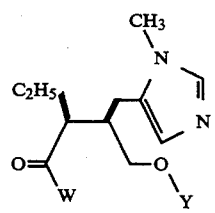

A) Y is hydrogen or

wherein R is selected from the group consisting of hydrogen;
C$_1$-C$_{18}$-alkyl;
C$_2$-C$_{18}$-alkenyl;
C$_2$-C$_{18}$-alkynyl;
C$_3$-C$_7$-cycloalkyl;
C$_3$-C$_7$-cycloalkenyl;
lower alkyl substituted C$_3$-C$_7$-cycloalkyl and C$_3$-C$_7$-cycloalkenyl;
aryl;
aryl lower alkyl;
aryl and aryl lower alkyl substituted by a substituent selected from the group consisting of lower alkyl;
lower alkoxy, nitro and halogen,
and W is the group

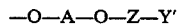

wherein Y' has the meaning of hydrogen or the group

wherein R' has the meaning of R above, whereby R' is the same as or different from R, A is selected from the group consisting of
C$_1$-C$_{18}$-alkylene;
C$_2$-C$_{18}$-alkenylene;
C$_2$-C$_{18}$-alkynylene;
C$_1$-C$_{18}$-alkylene; C$_2$-C$_{18}$ -alkenylene, and C$_2$-C$_{18}$-alkynylene which is substituted with a substituent selected from the group consisting of hydroxy, protected-hydroxy, C$_3$-C$_7$-cycloalkyl, C$_3$-C$_7$-cycloalkenyl, aryl and aryl lower alkyl, which cycloalkyl, cycloalkenyl, aryl and aryl lower alkyl groups are unsubstituted or substituted as defined above,
C$_3$-C$_7$-cycloalkylene;
C$_3$-C$_7$-cycloalkenylene;
lower alkyl substituted C$_3$-C$_7$-cycloalkylene and C$_3$-C$_7$-cycloalkenylene;
arylene;
arylene substituted by a substituent selected from the group consisting of lower alkyl, lower alkoxy, nitro and halogen;
alkylene, alkenylene, and alkynylene as defined above, which as a chain member contains the afore defined cycloalkylene, cycloalkenylene, or arylene group; and —Z—Y' is

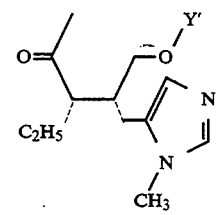

or

B) W is —OR, wherein R has the meaning given above, Y is

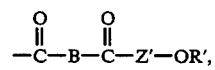

wherein R' has the meaning given above and B has the meaning given for A above, and —Z'—OR' is

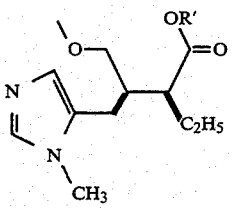

or

C) W and Y mean together (—W—Y—)

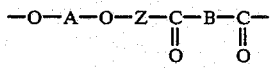

wherein A and B have the meaning given above and Z has the same meaning as in the group —Z—Y' above, or the acid addition salts of the said compounds.

2. Bispilocarpic acid derivative according to claim 1A, wherein wherein Y is —C(=O)—R, and R is $C_1$–$C_4$-alkyl, $C_3C_6$-cycloalkyl, benzyl or phenyl, and A is 1,2-ethylene, 1,3-propylene or 1,4-butylene, which is unsubstituted or substituted with hydroxy, the group Y—O—, Y having the meaning given above, or with one or two methyl groups.

3. Bispilocarpic acid derivative according to claim 2, wherein Y is —C(=O)—R and R is $C_1$–$C_4$-alkyl, $C_3$–$C_6$-cycloalkyl or phenyl, and A is ethylene, or A is 1,3-propylene, which is unsubstituted or substituted in its 2-position with hydroxy, the group Y-0- wherein Y has the meaning given, or with one or two methyl groups.

4. Bispilocarpic acid derivative according to claim 2, which is

O,O'-dicyclopropylcarbonyl (1,2-ethylene) bispilocarpate
O,O'-dicyclobutylcarbonyl (1,2-ethylene) bispilocarpate
O,O'-dicyclopropylcarbonyl (1,3-propylene) bispilocarpate
O,O'-dicyclobutylcarbonyl (1,3-propylene) bispilocarpate
O,O'-dicyclopropylcarbonyl (2-methyl-1,3-propylene) bispilocarpate
O,O'-dicyclopropylcarbonyl (2,2-dimethyl-1,3-propylene) bispilocarpate
O,O'-dipropionyl (1,3-propylene) bispilocarpate
O,O'-dicyclopropylcarbonyl (2-hydroxy-1,3-propylene) bispilocarpate
O,O'-dicyclopropylcarbonyl (2-cyclopropylcarbonyloxy-1,3propylene) bispilocarpate
O,O'-dipivalyl (1,2-ethylene) bispilocarpate
O,O'-dipivalyl (1,3-propylene) bispilocarpate
O,O'-di(1-methylcyclopropylcarbonyl) (1,2-ethylene) bispilocarpate
O,O'-dicyclopentylcarbonyl (1,2-ethylene) bispilocarpate
O,O'-dipropionyl (1,2-ethylene) bispilocarpate
O,O'-diisobutyryl (1,2-ethylene) bispilocarpate
O,O'-dipropionyl (2-hydroxy-1,3-propylene) bispilocarpate
O,O'-dicyclohexylcarbonyl (1,2-ethylene) bispilocarpate
O,O'-dicyclopentylcarbonyl (1,3-propylene) bispilocarpate
O,O'-dicyclohexylcarbonyl (1,3-propylene) bispilocarpate
O,O'-dibenzoyl (1,2-ethylene) bispilocarpate
O,O'-dibenzoyl (1,2-propylene) bispilocarpate.

5. Bispilocarpic acid derivative according to claim 1B, wherein W is OR, wherein R has the meaning of $C_1$–$C_4$-alkyl, $C_3$–$C_6$-cycloalkyl, benzyl or phenyl, and B is 1,2-ethylene, 1,3-propylene or 1,4-butylene, which is unsubstituted or substituted with hydroxy, the group Y—O—, Y having the meaning given above, or with one or two methylene groups.

6. Bispilocarpic acid derivative according to claim 5, wherein R has the meaning of $C_1$–$C_4$-alkyl or $C_3$–$C_6$-cycloalkyl, and B is 1,2-ethylene, 1,3-propylene or 1,4-butylene.

7. Bispilocarpic acid derivative according to claim 5, which is

O,O'-succinyl (diethyl) bispilocarpate
O,O'-succinyl (diisopropyl) bispilocarpate
O,O'-succinyl (di-t-butyl) bispilocarpate
O,O'-succinyl (dicyclopropyl) bispilocarpate
O,O'-succinyl (dicyclobutyl) bispilocarpate
O,O'-glutaryl (diisopropyl) bispilocarpate
O,O'-glutaryl (di-t-butyl) bispilocarpate
O,O'-glutaryl (dicyclopropyl) bispilocarpate
O,O'-glutaryl (dicyclobutyl) bispilocarpate.

8. Bispilocarpic acid derivative according to claim 1A which is a (xylylene) bispilocarpate.

9. Bispilocarpic acid derivative according to claim 1 which is selected from the group consisting of O,O'-dihydrogen (1,4-, 1,3-, 1,2-xylylene)-, —(1,3-propylene)-, -(1,5-pentylene)-, -(1,6-hexylene) and -(1,7-heptylene) bispilocarpate.

10. Bispilocarpic acid derivative according to claim 1 which is selected from the group consisting of O,O'-diacetyl-, O,O'-dipropionyl-, O,O'-dibutyryl-, O,O'-divaleryl-, O,O'-dibenzoyl- and O,O'-dicyclopropylcarbonyl (1,4-xylylene)-, -(1,5-pentylene)- and -(1,6-hexylene) bispilocarpate.

11. Bispilocarpic acid derivative according to claim 10 which is selected from the group consisting of O,O'-dipropionyl (1,4-xylylene) bispilocarpate, O,O'-dicyclopropylcarbonyl (1,4-xylylene) bispilocarpate and O,O'-dicyclopropylcarbonyl (1,6-hexylene) bispilocarpate.

12. Bispilocarpic acid derivative according to claim 1B which is a (dibenzyl) bispilocarpate.

13. Pharmaceutical composition comprising as the active agent a compound according to the formula I as defined in claim 1 and at least one pharmaceutically acceptable carrier.

* * * * *